United States Patent
Schulze et al.

(10) Patent No.: US 6,893,396 B2
(45) Date of Patent: May 17, 2005

(54) WIRELESS INTERNET BIO-TELEMETRY MONITORING SYSTEM AND INTERFACE

(75) Inventors: Arthur E. Schulze, Wharton, TX (US); Tommy G. Cooper, Friendswood, TX (US); Emil S. Macha, Sugar Land, TX (US)

(73) Assignee: i-Medik, Inc., Santa Fe, NM (US)

( * ) Notice: Subject to any disclaimer, the term of this patent is extended or adjusted under 35 U.S.C. 154(b) by 100 days.

(21) Appl. No.: 09/860,950

(22) Filed: May 18, 2001

(65) Prior Publication Data

US 2002/0019584 A1 Feb. 14, 2002

Related U.S. Application Data

(63) Continuation-in-part of application No. 09/516,645, filed on Mar. 1, 2000, now Pat. No. 6,443,890.

(51) Int. Cl.[7] .................................................. A61B 5/00
(52) U.S. Cl. ........................ 600/300; 128/903; 128/904; 128/920
(58) Field of Search ................................ 600/300, 301; 607/30, 32, 60; 128/903, 904; 705/2, 3

(56) References Cited

U.S. PATENT DOCUMENTS

| | | | | |
|---|---|---|---|---|
| 5,544,661 A | | 8/1996 | Davis et al. ................. | 128/700 |
| 5,678,562 A | * | 10/1997 | Sellers ........................ | 128/904 |
| 5,899,855 A | | 5/1999 | Brown ........................ | 600/301 |
| 6,154,668 A | * | 11/2000 | Pedersen et al. ............. | 600/300 |
| 6,225,901 B1 | * | 5/2001 | Kail, IV ...................... | 128/903 |
| 6,234,964 B1 | | 5/2001 | Iliff ............................. | 600/300 |
| 6,245,013 B1 | | 6/2001 | Minoz et al. ................. | 600/300 |
| 6,250,309 B1 | * | 6/2001 | Krichen et al. .............. | 600/300 |
| 6,254,536 B1 | | 7/2001 | DeVito ........................ | 600/300 |
| 6,278,999 B1 | * | 8/2001 | Knapp ........................... | 705/2 |
| 6,292,698 B1 | * | 9/2001 | Duffin et al. ................ | 607/32 |
| 6,398,727 B1 | * | 6/2002 | Bui et al. .................... | 128/904 |
| 6,442,433 B1 | * | 8/2002 | Linberg ....................... | 607/60 |
| 6,443,890 B1 | * | 9/2002 | Schulze et al. ............. | 600/300 |

* cited by examiner

*Primary Examiner*—Eric F. Winakur
(74) *Attorney, Agent, or Firm*—Roberts, Abokhair & Mardula, LLC

(57) ABSTRACT

A system and method for monitoring patient variables in a wireless manner via a patient worn monitoring device is disclosed. The patient monitoring device is wearable and connects to a variety of sensors with at least one microphone for voice communications. The device connects to a wireless network and thence to the Internet for transmitting data to a Host for access by a medical care provider. The medical care provider communicates with the patient-wearable device via the Internet and the wireless network to send instructions to the patient-wearable monitoring unit and to communicate via voice with the patient. The medical care provider can also flexibly reconfigure the device to change collection parameters. When an alarm limit is exceeded as detected by the sensors, the data are transmitted to the Host computer for use by the medical care provider, thereby allowing full mobility to the patient wearing the device.

75 Claims, 8 Drawing Sheets

WIRELESS INTERNET BIO-TELEMETRY MONITORING SYSTEM AND INTERFACE

RELATIONSHIP TO PRIOR APPLICATIONS

This application is a continuation-in-part of U.S. application Ser. No. 09/516,645, filed on Mar. 1, 2000, now U.S. Pat. No. 6,443,890, herein incorporated in its entirety, from which priority is claimed under 37 C.F.R. 120.

FIELD OF THE INVENTION

This invention relates generally to medical monitoring devices. More particularly the present invention is a system and method for monitoring physiologic, biochemical or biometric variables of an individual in a wireless mode over the Internet.

BACKGROUND OF THE INVENTION

Monitoring devices of various types to monitor patient physiologic, biochemical or biometric variables have long been used by the medical community. A plethora of testing and monitoring equipment has moved out of the hospital into the doctors' offices and, in some cases, these systems have even progressed into home monitoring systems.

While these devices have clearly been extremely useful, many of these devices require that a patient be located at home, or in close proximity to a telephone system such that results of the monitoring can be transmitted over the Public Switched Telephone Network (PSTN) to some form of analysis center. Such devices do not necessarily lend themselves to the mobile life style in which many individuals find themselves.

For example, it is difficult for a busy person to stop in the middle of the day, proceed to a monitoring station, whether in a home or in some office, take the appropriate measurements, and then proceed with the business of the day. This is simply not possible and adds a level of stress to the already stressful situation of having to monitor physiologic, biochemical or biometric signals. For a seriously ill person, it is often very difficult for the person to move to a personal computer or to attach a monitor to a connection to the PSTN system.

What would truly be useful is a system for monitoring physiologic, biochemical or biometric characteristics of an individual on a mobile basis. Such a system would require little, if any, interaction with a monitoring device. Signals that are collected would then be sent in an automated manner to an analysis center or a physician's office. Alternatively, a physician could interrogate the system worn by a patient while the patient is mobile to obtain the physiologic signals of interest or create changeable automatic signal acquisition protocols depending on the patient's condition. Additionally, if more appropriate in a particular clinical setting, the patient could initiate sending of a signal to the physician.

SUMMARY OF THE INVENTION

It is therefore an objective of the present invention to remotely monitor physiologic, biochemical, or biometric variables from any patient.

It is a further objective of the present invention to monitor physiologic, biochemical, or biometric variables of a patient whether the patient is ambulatory or stationary when the health care provider is remote from the patient.

It is yet another objective of the present invention to monitor physiologic, biochemical or biometric variables using the Internet.

It is still another objective of the present invention to monitor physiologic variables in conjunction with a wireless communication device such as a cellular telephone.

It is a further objective of the present invention to monitor physiologic variables in a wireless manner within a generalized geographic area.

It is a further objective of the present invention to monitor physiologic variables without the patient having to proceed to any centralized location in a geographic area.

It is a further objective of the present invention to monitor a patient anywhere in the coverage map of a cellular- or satellite-based telephone network.

It is a further objective of the present invention to have data relating to physiologic variables automatically sent over a wireless network to a physician or other medical caregiver using the Internet.

It is a further objective of the present invention to allow a health care provider to interrogate the physiologic monitoring device in a wireless fashion using prescribed protocols or ad hoc queries whenever the health care provider needs to take such physiologic measurements.

It is a further objective of the present invention to provide voice communications in a wireless mode to and from a user and a medical caregiver.

It is yet another objective of the present invention to provide voice communications through a cellular telephone between a user and a medical caregiver.

It is still another objective of the present invention to provide two-way messaging between a user and a medical caregiver.

It is yet another objective of the present invention to detect a persistent out of range physiologic, biochemical or biometric measurement and to issue an alarm signal to the patient and health care provider.

It is a further objective of the present invention to have a "panic" function which allows both a user to send a "panic" message to a health care provider or allows a health care provider, after monitoring physiologic signals, to send a voice "advice" message or text-based instructions to the patient.

It is still another objective of the present invention to provide automatic testing and troubleshooting functions for the physiological monitoring device.

It is a further objective of the present invention to accomplish all the above objectives using a device that is worn by the patient in a relatively unobtrusive fashion.

These and other objectives of the present invention will become apparent to those skilled in the art from a review of the specification that follows. The words physician, doctor, healthcare provider, caregiver, medical care provider, care provider, etc. as used herein shall mean the person with the responsibility for the care of the patient.

The present invention is a Wireless Internet Bio-telemetry Monitoring System (WIBMS). The system makes use of a variety of physiological, biometric and biochemical sensors and measurement systems that are generally used to detect signals or measure variables directly from the human body or from biological fluids such as blood or urine. One such sensor system is described in U.S. Pat. No. 5,673,692 whose characteristics are incorporated herein by reference in their entirety. However, this particular sensor is not meant as a limitation. Literally any type of bio-sensor or physical sensor generally known to those skilled in the art will find use in the present invention. Further, the sensor of U.S. Pat. No. 5,673,692 can include a microphone so that the voice of the patient can be transmitted using the system of the present invention.

The physiological, biochemical, or biometric sensors are connected to a combination data acquisition module and wireless transceiver that is worn by the patient or placed conveniently near the patient. This combination sensor package and communication unit is known as the Portable Data Monitor, or PDM. The PDM can monitor many patient variables at once. The PDM is battery-powered and may operate connected to an external power adapter. The batteries that power the PDM can be single-use batteries or rechargeable batteries. Further, when the individual is in a mobile state, the batteries of the PDM, if rechargeable, can be recharged by plugging them into a car power outlet or into a normal AC outlet. This allows the individual to keep batteries constantly charged in the PDM whether the individual is mobile or in an office.

As noted above, the PDM is a patient-worn or patient carried (i.e., patient-wearable) device that allows maximum mobility to the particular patient.

The PDM has the ability, on a periodic basis, to interrogate physiological, biochemical and biometric sensors or measurement systems worn or located near the patient and to store signals from the physiologic, biochemical and biometric sensors or measurement systems. As required, in response to a physician query, on a periodic basis dictated by a protocol maintained on an internet Host, or a patient action, the PDM calls into a wireless network and transmits the bio-sensor information to the wireless network. The bio-sensor information then proceeds from the wireless network to the Internet and then to the Host, such as an analysis center or a data warehouse which receives and stores the information for subsequent analysis. In another embodiment, the PDM can be plugged into a cell phone or computer, adding the capabilities of such devices to those of the PDM. The PDM also comprises an emergency "panic" button whereby a patient can direct the transceiver portion of the PDM automatically to call 911 or a designated medical caregiver in the event of a medical emergency.

As noted above, the PDM is connected to various physiologic, biochemical and biometric sensors and measurement systems. Therefore, the PDM has sensor condition detection circuitry, connected to a lamp and/or a message display, which allows a user to determine that all sensors are operating correctly. When a sensor receives a particular signal out of the normal physiologic range for the particular patient and the out of range measurement is persistent, a sound and light alarm can be actuated such that the caregiver can understand that a significant medical event is occurring. The patient is also notified that an alarm condition is present. Simultaneously with such an alarm, a time-tagged record is recorded for subsequent retrieval and analysis.

Thus, when the PDM is functioning in a data acquisition mode, it receives information from the sensors, performs some limited analysis on that information and notifies the patient and caregiver of any non-standard conditions.

When the PDM periodically sends stored signals from the biosensor over the network, a unique identifier is encoded with any such data that is sent such that the data can be directly associated with a particular patient. The data and patient identity are secured.

Once data is received at the server, the data is stored with appropriate privacy and security issues dealt with in a manner known to those skilled in the art.

The PDM also comprises circuitry for self-testing its various sub-systems and sensors and for communicating any trouble shooting information directly to the patient in the event that the sensor becomes dislodged, for example.

Further, such trouble-shooting data can also be sent in a wireless mode to the central server such that trouble-shooting can take place remotely, or in the alternative, a new PDM unit can be sent to the patient. The patient may further connect the PDM to a personal computer (PC) for advanced servicing performed by a technician at a remote location.

The PDM also can be preset before giving it to a patient. In addition, and depending upon the biological signals being monitored, alarms can be set remotely by the health care provider over the Internet and subsequently via the wireless network and can be based upon the caregiver's knowledge of the condition of the patient. Such remote setting also occurs via the two-way communication of the transceiver portion of the PDM.

Communication rates of the WIBMS are optimized to fit common cellular calling and rate plans and to minimize the cost and air-time usage.

With the WIBMS, the following types of monitoring can take place:

digitally sampled electrocardiogram patient body temperature pulse oximetry pulse rate other physiologic, biometric, or biochemical variables, such as blood glucose, respiration, weight, etc.

various pre set alarm conditions or physiologic variables event occurrences per patient action/input.

As also noted above the PDM has bidirectional communication capability and has the capability to transmit "panic" signal over wireless or cellular network, to initiate 911 calls, to allow a patient-initiated voice calling over a cellular telephone link, and to allow medical provider voice calling to the patient over a cellular telephone link.

Other characteristics of the present invention will become apparent to those skilled in the art by review of the detailed description of the invention that follows.

DETAILED DESCRIPTION OF THE INVENTION

As noted above, the present invention is a Wireless Internet Bio-telemetry Monitoring System comprising a patient monitoring device which is conveniently worn or used by a patient and which interfaces with sensors together with a combination network that allows biologic signals or measurements to be reviewed and acted upon by a health care provider who is located remotely from the patient. Data from the monitoring system is sent in a wireless mode over a cellular network to the Internet, and then to a data analysis center (Host) for retrieval and review by a medical care provider.

Figure 1A:
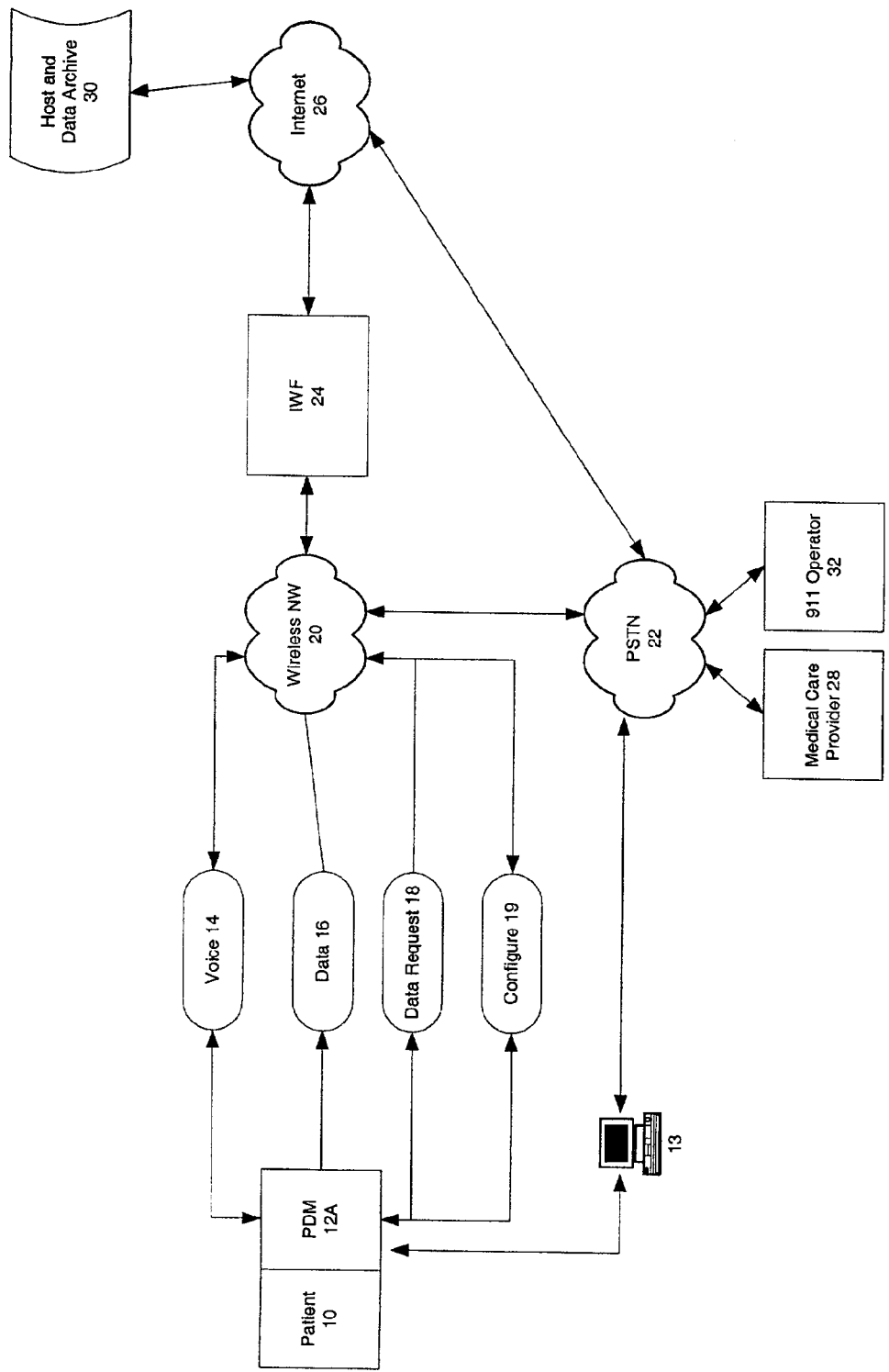
FIG. 1A illustrates one configuration of the Wireless Internet Bio-Telemetry Monitoring System (WIBMS).
Figure 1B:
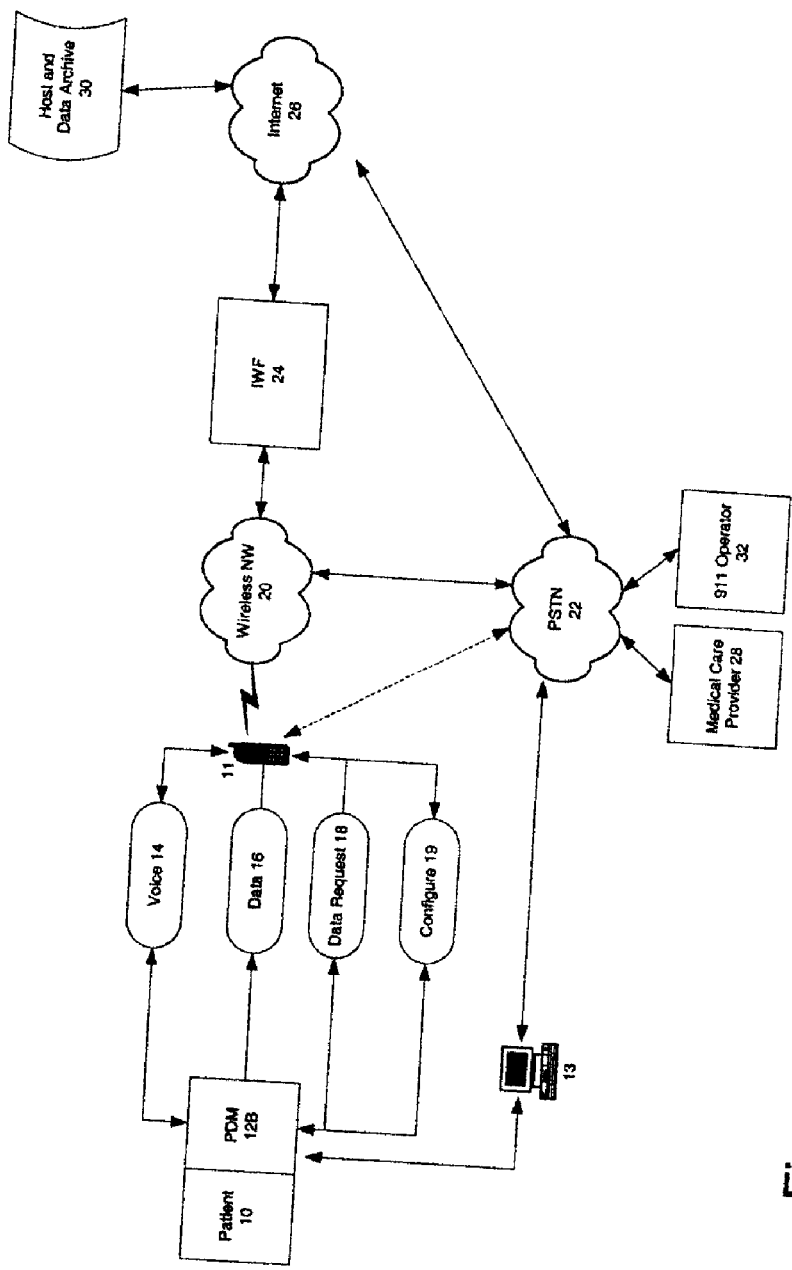
FIG. 1B illustrates an alternative configuration of the Wireless Internet Bio-telemetry Monitoring System (WIBMS).
Figure 2:
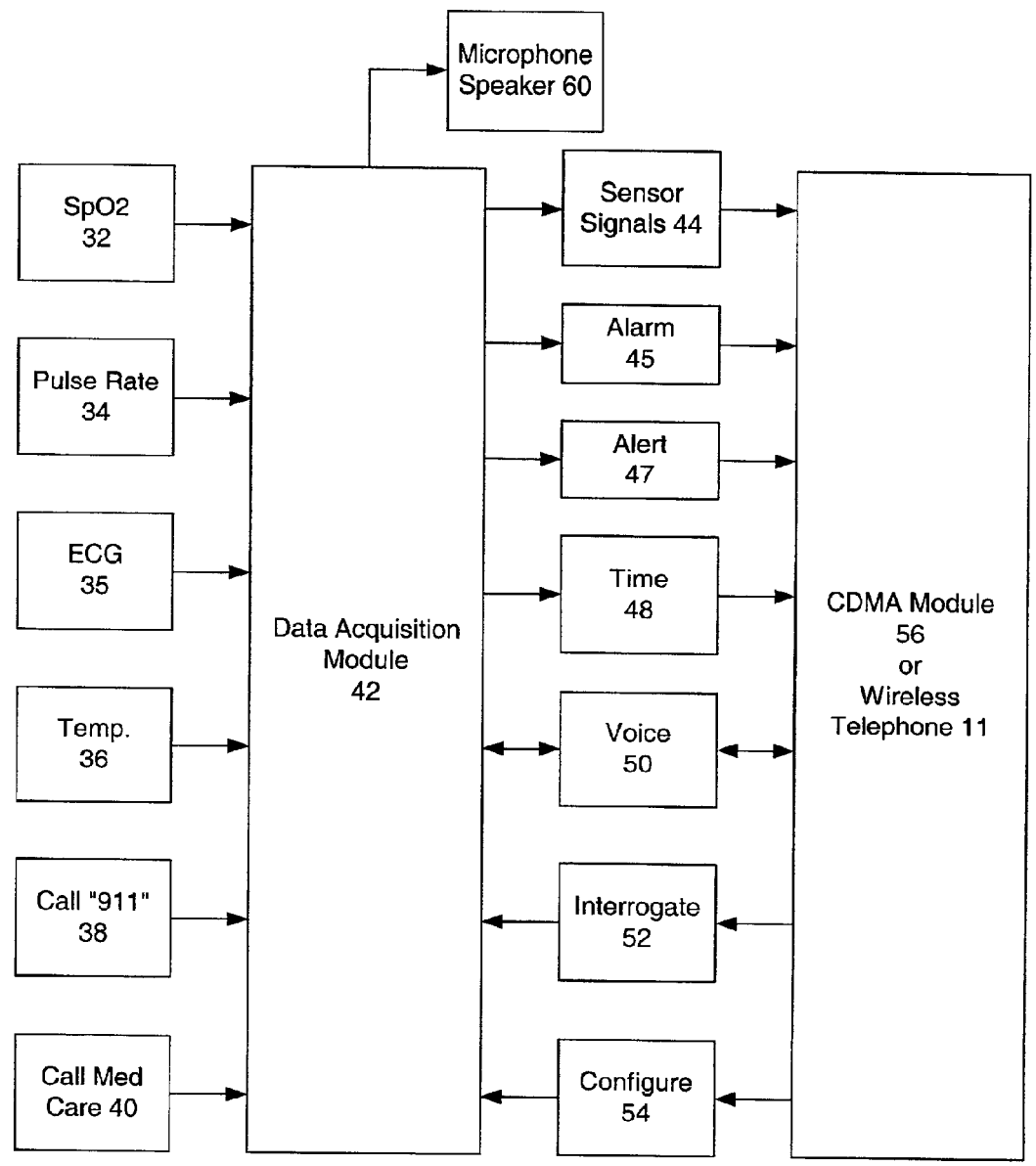
FIG. 2 illustrates the multi-variable patient monitoring portion of the WIBMS

In FIG. 1A, one embodiment of the Wireless Internet Bio-telemetry Monitoring System (WIBMS) is illustrated. Patient 10 wears a multi-variable portable data monitor (PDM) 12A. This PDM monitors a variety of physiological signals of a patient as further noted below. The PDM 12A has the capability of communicating bi-directionally via voice 14 in much the same manner as a normal cellular telephone. In addition, the PDM 12A sends data 16 on a periodic basis, or in some cases on a continuous real-time basis, over a wireless network to the Internet and then to a Host as well as receives requests for data 18 which may be made by a medical care provider over the Internet using wireless, PSTN, or alternative connections to the Host. The PDM 12A sends and receives data with or without use of the voice communication capability of the device. Alternatively, as in FIG. 1B, a cellular telephone 11 can further be plugged into the PDM 12B to replace the CDMA module 56 as shown in FIG. 2.

Wireless network 20 is the normal cellular telephone network currently in use. This type of network is not however meant as a limitation. For example PCS networks and other types of wireless loop networks are also suitable for transmission of the voice and data envisioned by the present invention. It will be apparent to those skilled in the art that such other networks can satisfy the requirements for transmission of voice 14, data 16, and request for data 18 to and from patient 10.

Once physiologic, biochemical or biometric data are transmitted over network 20, they are then transmitted via an Internetworking Function (IWF)® 24, for example, to preferably the Internet 26 for subsequent communication over the Internet 26 to the Host 30 for retrieval and review by the medical care provider 28. In addition, data can be archived again via the Internet 26 to a data archiving and distribution facility or Host 30. Data that is archived is stored in a private and secure fashion using techniques known in the art that allow secure transmission and access limitation.

In the event that voice traffic is being transmitted from the patient, a wireless network 20 connects to the public switched telephone network 22 that connects to the medical care provider 28 or 911 operator 32. Again, in this fashion, the medical care provider 28 can receive voice information from the patient 10 and provide voice feedback to the patient 10 as well. Similarly, the medical care provider 28 can both receive traffic from the WIBMS as well as transmit requests for data over Internet 26 through IWF 24 over the wireless network 20 through the Internet 26 via the data repository/Host to the PDM 12A, 12B as well as configure 19 the PDM 12A, 12B.

The PDM 12A, 12B further provides audio, voice and text messaging capabilities. Voice messaging typically is short segment phrases, typically of two-second duration. Audio/voice messaging from the PDM 12A, 12B usually arises as the result of alarms and alerts detected and reported to the internal system status. There are some special occurrences such as when the patient instigates a local voice call. As such, messages will be presented to guide and inform the patient as to the call status.

When audio messages arise because of alarms/alerts reported by the internal status, it is desirable to repeat the messages until the error is resolved. This can be complicated when several are pending concurrently. Presenting distinctive sound patterns (for instance, a two-tone sequence) may relieve this in lieu of voice phrasing that can be intuitively associated with a particular error.

Two-way ext messaging between the PDM and the Host is typically provided via a touchscreen on the PDM and can be used for various purposes, as discussed later in reference to FIG. 6.

To further manage concurrent message situations, priority is given to each message according to the nature of the message. Messaging uses considerable battery power. Thus, audio message management is important for efficient use of the PDM power supply. Alarms have top priority. For situations where there are multiple alarms active, then the sequence can be configured to further set priority by the type of alarm, or create a timing cycle which displays each alarm for a short time period. Messages are displayed for a Low Battery Condition, Non-Recoverable Alerts, Voice Call guidance, and Recoverable Alerts (such as a sensor disconnection). Priority can also be set to manage multiple message situations for these types of messages.

All data that is received from the PDM 12A, 12B and the network is archived 30 so that the data from the specific patient can be monitored over time and analyzed for trends that can be used for alarm setting and data collection protocols. All such data is transmitted in an encrypted form with limited access using methods known in the art so that patent privacy and confidentiality is maintained.

In FIG. 2, the PDM is further illustrated. The PDM (initially noted as 12A in FIGS. 1 and 12B in FIG. 1B) comprises, without limitation, a number of biosensors. For example, blood oxygen saturation level 32, pulse rate 34, electrocardiogram (ECG) 35, and body temperature 36 can all be measured by physiological sensors associated with the appropriate measurement. Signals from the sensors are picked up and stored by the data acquisition module 42. This information from the biosensors is then sent as sensor signals 44 to the CDMA (although other protocols may also be used) module 56 of the PDM 12A for subsequent transmission. Alternatively, these signals can be sent by PDM 12B directly to the cellular telephone 11 as shown in FIG. 1B.

In addition to simply acquiring data, the data acquisition module 42 also notes any alarm condition 45 or alert condition 47 and transmits that information via CDMA module 56 or cellular telephone 11 to the Internet, where it can be accessed by medical care providers. In addition, data acquisition module 42 transmits the time of day 48 with any transmission of alarm information, alert information or sensor information. As noted earlier, the various alarm and alert conditions can be reconfigured by the health care provider over the Internet and the wireless network without any patient interaction.

The CDMA module 56 is, for example, one manufactured by Qualcomm for use as a cellular telephone module. The CDMA module 56 or cellular telephone 11, in connection with 3Com "Quick Connect" Internet connection software and 3Com Internetworking Function (IWF) device are all used to connect to, for example, the Sprint digital cellular telephone network. The characteristics of the Qualcomm CDMA cellular phone module, the 3Com Quick Connect Internet connection software, and the 3Com Internetworking Function device are all incorporated herein by reference in their entirety.

The CDMA module 56 or cellular telephone 11 currently allows for digital cellular communications at 14.4 kbps, which is sufficient for the transmission of the physiological, biochemical and biometric information contemplated by the present invention. This is not however meant as a limitation as further faster wireless modulated speeds will become available. All of these faster connections will be suitable for transmission of the data and voice of the present invention.

The PDM can communicate using any of three platforms of communication operation. These platforms are: CDMA Periodic Post, CDMA Host Request, and RS232 Slave Request. Only one platform operates at a given time. Data supplied by the PDM over these platforms may be a one-time snapshot, a sequence of various data, or a chain of real-time data.

In the CDMA periodic post communication, the PDM initiates a Quick Net Connect (QNC) call to establish connection to the Internet with Sprint-PCS as the Internet service provider (ISP). The PDM makes connection and validation to a Host website and posts data to an assigned server page in the Host system.

Profiles are stored at the PDM in non-volatile memory. Each profile contains multiple parameters, one of which determines how often the PDM is to initiate a CDMA network connection to a specific website Host and post information to it. The specific types of data to be posted to the Website are also determined by information within the profiles. Various types of posting data may each be directed to specific web pages of the Host. The PDM post may contain zero or one piece of data. Each post is a separate transaction. The PDM waits for a response from each post transaction. The response may be a positive acknowledgment, ACK, or a negative, NAK. Host responses, posted at the Host in response to each PDM post transaction may contain additional information beyond an ACK or NAK. The situation where no data is posted is a mechanism where the Host can subsequently make a request to the PDM for a null data post in its response.

If more information is required, the Host will respond with and ACK+MORE message. This type of response alerts the PDM to seek Host requests on the assigned server page. If no more information is required and the post was successful, an ACK+NULL response is given. If more data is required, the PDM responds to the additional Host requests before reverting back to its original list of post items. If the last post results in an ACK+NULL, the PDM CDMA connection is ended.

If a NAK is the response to the PDM post, the PDM tries to post the data a predetermined number of times until the post is successful or until the number of tries is exhausted. If the PDM was unsuccessful in its post attempts, it pauses for a predetermined length of time as defined in the profile in effect and then tries to post anew. A NAK may also be accompanied with an error reason. There is logic in the PDM to interrupt the error reason and take appropriate action. For example, insufficient CDMA signal error will result in the termination of the current post attempt.

The second communication platform used by the PDM is a CDMA Host Request. A CDMA Host Request is performed by a Host making the data request of a specific PDM. A Host is any web site server capable of uploading profiles and operational parameters to the PDM. Some Hosts will download and store patient data. Other Hosts may be used to service the PDM remotely. The Host initiates a CDMA voice call to a specific PDM. The PDM is awakened by the incoming ring. The patient is not initially alerted to the incoming call. The PDM responds as follows. First, it reads the incoming caller ID, if available, and determines if it is coming from a known Host or from a voice originating point. If the call is from a voice origination point, then the PDM logs the originating point as a CDMA voice call, alerts the patient by allowing the handset to ring and the patient answers the call.

If the call is from a specific data origination point Host, then the PDM waits for the Host Site to finish ringing and then rings back to initiate a CDMA QNC network connection with the Host website. Because the Host has originated the sequence, it must now make available an active server page, which contains an Internet address containing a table of requests that are expected to be serviced by the PDM. This table of request page is called the Active Request Page (ARP). The duty of the PDM is to go to the Active Request Page and sequentially service the requests found at the page. For instance, the PDM may be requested to provide the user's temperature, SPO2, pulse rate, beat-to-beat variability, and single lead ECG reading. On completion of all requests, the PDM terminates the CDMA network connection.

An alternative method for the Host to initiate a request is for the Host to make a CDMA call to the PDM, and then hang up. There is no check of the caller ID. The PDM initiates a post to the Host web site with no data. The Host responds with an ACK+MORE which signals the PDM that requests are outstanding. The PDM then queries the Host for the active request page, (ARP). The PDM connects to ARP, retrieving the Host requests.

The third communication platform is the RS232 Slave Request. With this platform the PDM may be directly connected to a Host Device, such as a PC or laptop, using a direct cable connected between the Host Device Com port and the PDM. The PDM will be configured as data communications equipment, or "DCE". The PDM acts as a "slave" operating with this platform, because it responds only to requests sent to it by the Host. In this manner, the Host sends a request and then the PDM answers the request with specific information within a set period of time. The PDM can respond to only one request at a time. An existing request must be either totally completed or a timeout declared before a successive request can be issued.

An alternate or additional means of communication with the local Host is to use Infrared optical (IrDA) techniques. IrDA allows local communication between the PDM and a client device such as a desktop PC or laptop. IrDA may be used with or without cabling, thus removing the tether between the PDM and the local client. Another embodiment would provide RF communication between a local client such as a PC and the PDM, thus removing a line of sight requirement inherent with IrDA.

When the PDM is in a server or slave capacity to a local Host, the PDM must always be available. This arrangement requires relatively high power consumption by the PDM. It is preferable that the PDM be powered by an external power adapter under these conditions.

The local connection between client device and PDM (slave or server) platform has several uses. It is used in manufacturing for manufacturing tests and special servicing. It can be used in the field for downloading programs. It can be used in the field for refurbishment of the device, which includes cleaning of data memory, time setting, and controlling basic operating states. With this platform, a Host separate from the Host gathering user data can be used to provide servicing functions.

Because the PDM can communicate with these different platforms, several functions can be performed with the PDM. The PDM will support the following list of communication request types, at a minimum. Actual request transactions could include a concatenation of more than one these types. CDMA Host platform requests and RS232 platform requests are communicated over the same serial port. Only one of these platforms may operate at a given time. The PDM has logic to detect the type of cabling associated with the serial port, thus responding in an appropriate manner. Distinctions between CDMA Host Request and RS232 platforms are included within the list as shown below:

1. Setting the Real Time Clock (RTC) with time and date, and retrieving RTC time and date from the PDM. A recommended format for RTC is Greenwich Mean Time (GMT).
2. Retrieving and Setting of Patient identification data. Patient Identification data consists of 128 bytes of free format ASCII data representing some description of the user/patient.
3. Retrieving and Setting of a Patient ID number. Such a number is an alias for the patient's actual name, and functions as a security measure.
4. Retrieving and Setting of the PDM's operational profile(s). It is permissible to consider sending/receiving all profiles at once, or as separate profiles. Checksum operation should accompany the transmission of profiles.
5. Retrieving the PDM's internal status.
6. Setting the PDM operational mode from a remote location. Among these, for example and without limitation, are power-ON/power-OFF, sleep/awake, idle, run, alarm, and the like.
7. Retrieving the PDM manufacturing data, such as hardware serial number, software revision, unit type or class, build identification, and other like data. Setting of this data is permissible with only the RS232 platform.
8. Retrieving the PDM telecommunications data such as the assigned telephone number, IP address, etc. Setting of this data is permissible with only the RS232 platform.
9. Retrieving and Setting of telephone call numbers. A Repository and Host Site telephone number, the Host Site URL address/password, and the Voice telephone number to use for emergency calling (such as with the panic button) are examples, without limitation, of important call numbers that users and caregivers would need readily available.
10. Retrieving of both the Most Oldest and the Most Current patient data records from logged memory by index numbers.
11. Retrieving of a patient record specified by its index within logged memory.
12. Retrieving of the most current data record as output by the PDM. Timed periodic data retrieval using this technique can allow continuous real-time waveform data transfer to a Host device.
13. Erasing logged data. With separate special request, the entire logging memory may be erased.
14. Performing the Reset of Alarms within the unit.
15. Performing the Reset of Alerts within the unit.
16. Retrieving and resetting voice call/data call instances and on-air accumulative time statistics.
17. Using the RS232 platform only, the unit firmware can be downloaded and programmed into the PDM by a Host device. Correspondingly, such firmware can be uploaded for verification.
18. Using the RS232 platform only, the unit's voice synthesis sound set can be downloaded into the PDM by a Host device. Correspondingly, a sound set may be uploaded for verification.
19. Using the RS232 platform only, diagnostic and special loading firmware may be downloaded and programmed into the PDM by a Host device. Correspondingly, such firmware may be uploaded for verification.
20. Using the RS232 platform only, a special, protected request can be sent to the PDM from a Host device. The special request cleans all operational profiles to a default state, resets all alarms and alerts, erases all memory and patient data, and places the unit in IDLE mode. Such a request that causes multiple actions is useful for the healthcare provider to refurbish the unit for the next outgoing patient.
21. Instigating a specific audible sound phrase or tone of the voice synthesizer can be done from a Host device. Such requests can be used to alert the patient under unusual conditions. Such requests also serve as diagnostic tools to ensure the PDM is working properly.
22. Using the RS232 platform only, special diagnostic request may be issued from the Host device for test purposes. For example, a request may be sent to provide raw data from a measurement system.

Data that is collected is encrypted to prevent eavesdropping or tampering with any commands. All information and data is Internet protocol compatible and contains error checking to insure data accuracy.

The data acquisition module 42 continuously monitors, for example and without limitation, ECG and transmits that information from the PDM to the Internet. Transmission of data can be in real time and/or can be stored and forwarded depending upon the collection protocol ordered by the medical service provider. Similarly, temperature measurement, pulse oximetry, and pulse rate all can be collected and transmitted continuously during various periods of time or can be collected stored and burst transmitted over the wireless network as required.

Measurement systems data is collected, reduced and stored to recording memory on a per second basis. If an operating profile calls for particular measurement duration of X seconds, then X successive logging records are produced during the X seconds. Note that the different measurement systems may be specified with interval times and duration that are not necessarily in synchronization with others. To resolve this difference in measurement data, data collection can be programmed in sums of the aggregate of all interval times and duration together to derive an aggregate interval time and duration. The Host that generates the operating profiles must come up with efficient schemes for specifying the measurement intervals and duration collectively.

The timekeeping mechanism for determining when a measurement recording is to take place is the Real-Time Clock (RTC) that provides time 48. Each stored record of measurements contains a time stamp and the current internal status of the PDM.

When the PDM enters the Alarm Mode (discussed in more detail below), all measurement data is recorded continually with once a second records until relieved by a communication request. Recording Data Memory 594 (see FIG. 5) is constrained by storage capacity in a small and portable device. Therefore, it will typically be arranged as a wrap-around memory. It is cautionary to note that when memory becomes full, the recording process continues with the oldest data becoming overwritten.

Pointers and indexers manage Recording Data Memory 594. As such, the Recording Data Memory 594 along with its pointers and indexers are non-volatile. Indexers allow a Host System to request and retrieve any particular logging record via communication interface. Patient recording memory is allocated in buffers of size a multiple 16, up to a 1K buffer (1024 bytes). Another embodiment would store records of one size in one area of memory and buffers of another size in a unique section of memory. If the measurement system only contained discrete data (i.e., integers) then the buffer size could be uniformly 16 bytes. If, however, the data was a mix of discrete and analog information (e.g., waveforms) the records might have to have buffers of mixed sizes. For example, 16-byte records might be used for pulse rate and 128-byte records for ECG information.

Records are chronologically sequenced within regions, the lowest numbered records being the oldest. The 16-byte records would contain a time stamp plus the discrete data plus the PDM's internal status at the particular time stamp. Whereas a waveform record would only have a timestamp and the waveform analog representation in that record. Records would not have negative timestamps. A waveform record will always have a corresponding discrete record associated with the waveform record. The corollary, a discrete record will always have a waveform record associated with it, may not be true.

There is a finite amount of patient recording memory and thus the records wrap in memory. That is, the eldest records are overwritten with current records when the record memory area is full. The wrap points are maintained, thus creating a virtual chronologically sequenced record memory.

The data acquisition module 42 contains logic that allows an "alarm" condition to be transmitted at any time whenever the alarm criteria are fulfilled. Further, any alarm condition must be reset by the health care provider by directing the Host clear the alarm through the Internet and then over the wireless network. Any "sensor off" signals 62, occurring for example when a sensor is turned off, broken, or has become disconnected, is sent upon occurrence. The patient is alerted to take appropriate action, such as replacing or repairing the sensor. While such information is transmitted by the data acquisition module 42 to the CDMA module 56 (or cellular telephone 11) and thence to the wireless network, a voice synthesizer or other sound generator also provides an audible alert to speaker 60 to the patient that a particular alarm or sensor off condition has occurred.

As noted earlier, the patient using the PDM also has the capability to automatically (or speed dial) 911 as needed. Data acquisition module 42 also processes this information and passes it over a voice connection 50 to CDMA module 56 and thereafter to the wireless network for communication.

The patient also has the ability to call 40 the medical care provider (i.e., 28) on a non-emergency basis. This is accomplished by a dedicated function speed dial "button" on the PDM. Again, data acquisition module 42 processes voice information 50 and passes that information to the CDMA module 56. The PDM has voice call capability with use of the CDMA phone. The user can instigate such calls with buttons on the PDM front panel. The PDM further has an auto-dial capability. The PDM stores and accesses a table of voice call phone numbers to make automatic dialing calls when the front panel buttons are depressed. Likewise, the front panel buttons are also used to terminate (hang-up) a voice call. Two types of automatic call dialing can be performed. A call can be made to a specifically stored voice number, such as a health care provider via 40. A call 38 can also be made to emergency services, such as a 911 call.

The data acquisition module 42 assigns priority to voice calls over CDMA data calls. When a voice call is instigated by the patient, any data calls in process will be terminated. A voice call instigated by the Host when data is being posted will fail until the PDM post is finished. The health care provider may instigate a voice call. The PDM has logic to distinguish between a CDMA Host request and a voice call.

As previously discussed, the data acquisition module contains logic that allows an "alarm" condition be transmitted at any time whenever alarm conditions are met. In the PDM, alarms and alerts cause the system to change modes and to inform the patient of the condition that caused the change. Alarms relate to one or more physiological measurements falling outside of set limits. As an additional safety feature the exceeded limits must persist for a specified minimum duration before the condition can be declared a tripped alarm (reducing false alarms).

Alarms are used to notify the patient and/or health care provider of patient conditions that require caregiver attention. Alarms are activated when a physiological measurement exceeds high or low limits for a prescribed time (persistence) period. Both the limits and the persistence period for each parameter are set by the caregiver and stored in the profile. The alarm for each parameter may be disabled by the caregiver with settings in the profile (See detailed profile description below). Once an alarm is activated, it can only be cleared by the Host. The measured parameter causing the alarm is recorded in PDM memory until the alarm mode is transitioned to idle mode (See FIG. 3 description). The PDM contacts the Host, which in turn contacts the caregiver with information. The voice message system is activated to inform the patient that an alarm condition has occurred.

Alerts relate to sensor errors or device hardware warning/malfunction. Alerts are used to inform the patient that the system is not operating properly and that corrective action is required If an alert is in force for a measured parameter, then any alarms associated with the parameter are not allowed to activate. There are two classes of alerts; (1) recoverable and (2) system failures Recoverable Alerts—These are alerts that may be corrected by the patient. Such an alert may be caused by a detached or disconnected sensor. The alert is cleared when the patient corrects the problem. Another example of a recoverable alert occurs when a PDM is out of RF signal range. Again, if the patient is informed about this, the signal range condition might be correctable. Still another example is 'battery low' which requires the patient to replace the batteries. A last example occurs when the recording memory becomes close to full. However, in such cases, it is the Host's responsibility to detect this alert and perform automatic measures to relieve it.

System Failures (or Non-Recoverable Alerts) are errors that can be associated with system problems, such as memory error or RTC error. Such alerts require technical intervention. The patient is must contact the caregiver via a voice call to get a replacement PDM.

As noted above, the medical service provider or other organization that is responsible for monitoring and maintaining of the PDM can interrogate 52 the data acquisition module 42 of the PDM. A request for information flows from the medical care provider over the Internet to the Host. The Host initiates a voice call to the PDM, which triggers the PDM to establish a data call back to the Host. Alternatively, the data acquisition module can be reconfigured 54 to update communications capabilities, or to change the protocol for frequency of monitoring physiologic data and alarm limits.

The PDM can be programmed to operate according to several different operating profiles. When operating, the PDM is governed by the Operating Profile in force at the time. One embodiment provides for three profiles. A fourth, profile, generated internally by the PDM, is the alarm profile which supercedes any other current profiles when an alarm condition occurs.

The PDM operates on a 24-hour-period basis. An operating profile therefore contains a start and stop time within the 24-hour cycle that determines when it is in force. The start and stop time is expressed in minutes after midnight. The maximum in-force time can be 24 hours when there is 24 hour's difference between start and stop time. The 24-hour profile might contain a start time of 0 and a stop time of 1440. The minimum in-force time can be 0 hours if start and stop times are the same. This configuration causes a profile to be inactive. While Start and Stop times are specified in minutes passed midnight as based on the RTC, any unambiguous start and stop time setting method will be sufficient. Profiles are set from a Host device.

Profiles can be engaged to cover a specific portion of the day if desired. For instance: Profile 1 could be assigned from midnight to 6 AM, Profile 2 could be assigned from 6 AM to 8 PM, and Profile 3 could be assigned from 8 PM to midnight. The Start and Stop time can span across midnight (for example start=10 PM, stop=2 AM).

Profiles can have start and stop time overlaps during the 24-hour period, thus permitting another dimension of flexibility. In such case, Profile 1 has greatest priority during an overlap, and Profile 3 has least priority. Profiles can be set for a portion of the day to have an absent profile assignment. When an absent profile is in force, and the unit does no measurement or recording.

Each profile contains a control block made up of multiple parameters. The following parameters and rules set comprise one embodiment of parameters, but is not meant to be a limitation. A Start and Stop Time is set in minutes. A Periodic Posting Period is set in minutes. The Periodic Posting Period is the periodic interval in which the PDM will attempt to post data to the Host Site. An Enable/Disable switch is set for each measurement system. Disable means that the particular measurement system will be put to sleep entirely while the profile is in force. A Measurement Interval Time (in seconds) is provided for each measurement system run by the PDM. This interval time determines the length of time between a measurement recording session. A Measurement Duration Time (in seconds) is set for each measurement system. For example, the ECG measurement may be data logged every 20 minutes for a measurement duration of 30 seconds. For this example, the measurement duration is set to 30 and the interval is set to 1200 seconds.

Several control block settings address alarms. Each measurement system has an alarm enable/disable switch. Each alarm will have a high and low limit value. However, exceptions to the limits can be set. Limits for each patient will be different, and must be interpreted by a caregiver. Each alarm will have an alarm persistence time set. Persistence time is the amount of time in seconds that an alarm condition must be breached continuously before it is declared tripped.

Another control setting is an Event Mode duration time. An 'Event' is discussed later in detail. When the patient pushing the Event button instigates an Event, the unit enters Event Mode for the duration time, then returns back to its previous Mode. Each profile contains check bytes. The check bytes must be verified on a periodic basis. It must also be verified when the profile is modified.

The profiles of the PDM are considered vital to operation and are stored in non-volatile memory. If the profiles are to be changed, the following is one embodiment for executing changes to the profiles. First, the profiles are retrieved from the PDM by making a Host request. Next, a check of validity is made using the check characters. Next the one or more profiles are edited for any parameter changes. New check character must also be provided in the profiles. A request is then made of the PDM to load the profiles. Check characters should also be loaded. The PDM loads the revised profiles and check character data into non-volatile memory. Flash memory usually serves as non-volatile memory. After flash memory has been modified, the Host requests profile status. The PDM response is checked for correct implementation of the profile changes.

Figure 3:
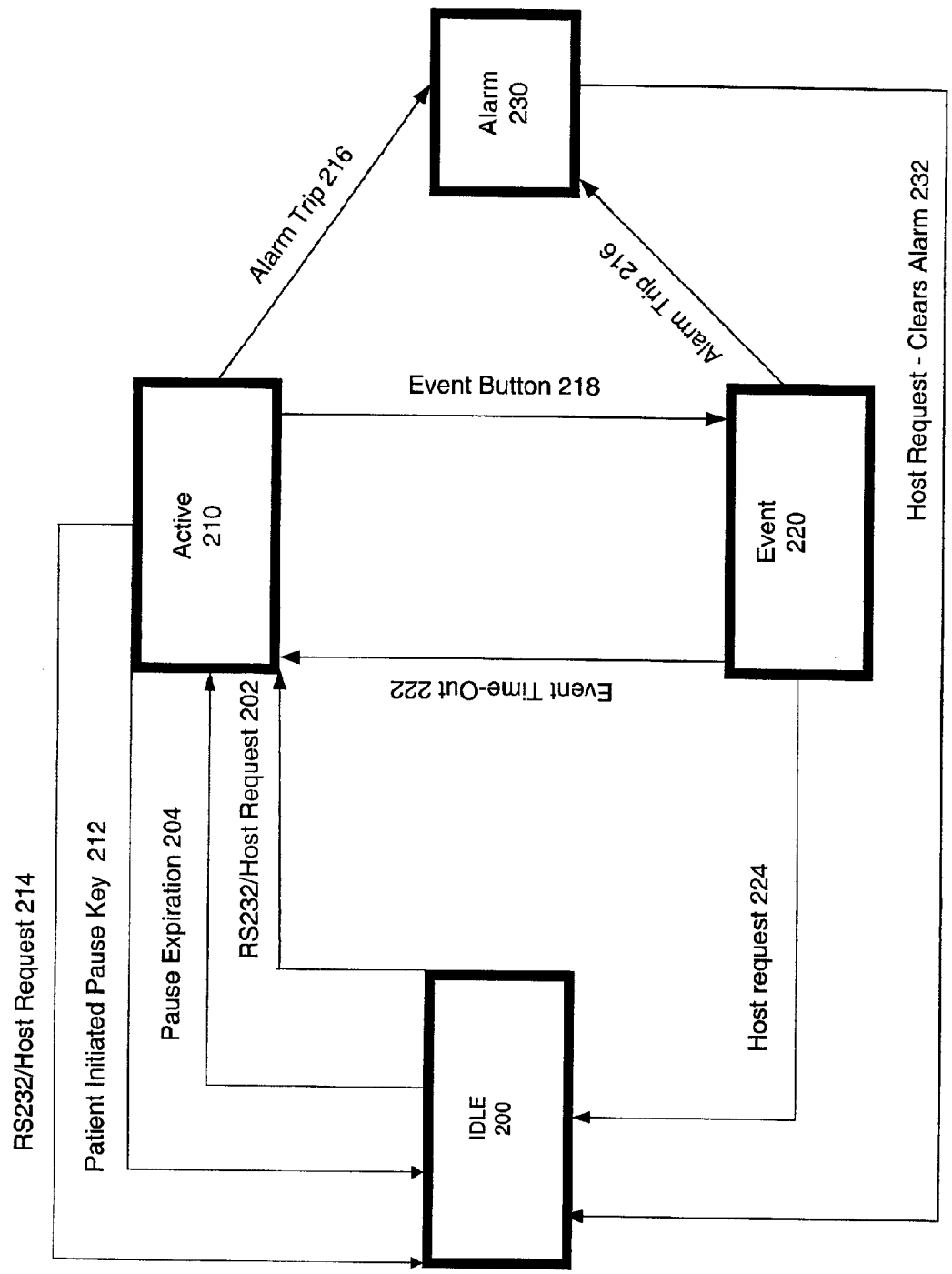
FIG. 3 illustrates the portable data monitor operational mode state transition model.

In FIG. 3, the PDM operational mode state transition model is illustrated.

The PDM operates according to four operational modes. They are: Idle Mode 200 Active Mode 210, Alarm Mode 230, and Event Mode 220. In Idle Mode 200, the profiles are disarmed and all alerts are disarmed. Transition to Idle Mode 200 can be initiated by the Host or the local PC or laptop via a RS232 connection. A patient-initiated transition 212 to Idle mode from Active mode is implemented when the patient depresses a pause key located on the face of the PDM unit. Pause key implementation is regulated by the profile in effect. Further, the transition to Idle Mode is of a fixed duration as set in the current profile. While the PDM is in Idle mode 200 the current profile is disabled and there is no data acquisition and no recoding. Further, even if in Idle mode because of a patient initiated pause, alarm and alert detection are disabled. A record is stored to recording memory at the start of the Pause, hence the status in the record will mark the pause. Return from Idle Mode 200 to Active mode 210 occurs at pause expiration 204.

Transition from an Alarm Mode to Idle Mode is via a Host request 232. This transition clears the alarm condition. Transition from Active Mode to Idle Mode, not pause key driven, is achieved via RS232/Host request 214 The PDM will respond to RS232/Host request to go active 202. Idle Mode is used when it is desired to modify operational profiles, set time, change the patient identification, etc. Once in Idle Mode, the PDM can only go to Active Mode by RS232/Host request 202 or by Pause Expiration 204.

Active Mode 210 is used whenever the PDM unit is fully performing the profile in force. Alarms as governed by the profile in force may be armed. All alerts are armed. The PDM can further change from Active Mode to Event mode 220 when Event Button initiated transition 218 occurs or to Alarm Mode when an Alarm trip 216 occurs Alarm Mode 230 operates once the unit has had an alarm trip 216 and transition occurs from Event mode or Active mode. During an alarm, data is continually being measured and logged. Logged data is identified as Alarm Mode data. Successive attempts are made to connect with the Host Site to post data. The Host Site should always check the internal status of the PDM for alarms. Voice messages or audible signals are generated during Alarm Mode. The current operational profile is "locked". That is, the unit will remain at the profile in which the trip occurred until the unit is forced into Idle Mode 200 by Host request 232. The alarm bits of the internal status are reset when the PDM is transitioned to Idle mode. This clears any alarms.

Event Mode 220 begins when the patient pushes the front panel Event button 218. Event Mode 220 preempts the Active Mode 210, but has a definite duration time when there is a transition back 222 to Active Mode 210. During Event Mode 220, data is continually being measured and logged. Logged data is identified as Event Mode data. If the patient depresses the Event Mode button and the unit is already in Event Mode then this will reinitialize the duration timer. Thus Event Mode duration is extended. From the Event Mode, the PDM can either return to Active Mode at expiration of Duration time 222 or go to Alarm mode if there is an alarm trip 216 or to Idle Mode by Host request 224.

The PDM further monitors its own internal status. The PDM records: (1) the status of measurement systems (active, disabled, etc.); (2) alarm status for each measurement system; (3) alert status; (4) current operation mode; (5) current profile in force; (6) communication signal status; and (7) recording memory status. Status will be preserved during power-down periods and restored on subsequent Power-On. This preservation requirement extends to abnormal power-down situations as well, such as an accidental power disconnection.

The PDM runs a power management system. The PDM detects low power, conserves power, runs safety checks, and alarms when power is interrupted. The PDM periodically monitors its battery voltage and indicates the current battery capacity at the front panel display with an indicator. At least two thresholds are checked. If the battery voltage falls below the first of these, then a low battery alert is active. If it falls below the second, then automatic power shutdown occurs. The unit must be able to anticipate if it has enough battery capacity to drive communications each time such communication is established.

The PDM runs a power conservation algorithm. The PDM has a modularized system and sub-system architecture such that those systems that are momentary or long-term idle can be either shut down or low-power throttled. If the voice synthesizer is not sending messages, then the voice synthesizer sub-system is shut down. If a particular measurement is not active, then that measurement subsystem is powered down.

Power conservation extends to the core processing system itself. Clocks and peripherals within this core are powered down or throttled down, if it can be done safely.

Safety measures include a "watchdog" system (see 599 in FIG. 5), a periodic crosscheck that assures that both the system clock and the RTC are operating normally. The PDM additionally runs a power-ON confidence test. The PDM contains a diagnostic program which can be invoked either with a special sequence of interaction with the front panel, or with requests via RS232 communication request port.

A Power Interruption Alarm is run by the PDM. The PDM contains an independent battery-powered alarm subsystem that monitors main power-on. If the main battery power to the PDM is interrupted while in the power-on condition, or if the PDM watchdog is tripped, then this subsystem will cause an audible alarm and set a condition in the internal status. The subsystem will remain in a tripped condition until the patient resets the alarm via front panel menu interaction, or the alarm is reset via a communication request.

The system of the present invention includes the network and can allow simultaneous operation of any number of PDMs. This system is only limited by the capacity of the wireless network to handle traffic. In the same fashion that a cellular telephone has a roaming capability, so does the PDM, therefore allowing continual transmission and updating of physiologic data.

Figure 4:
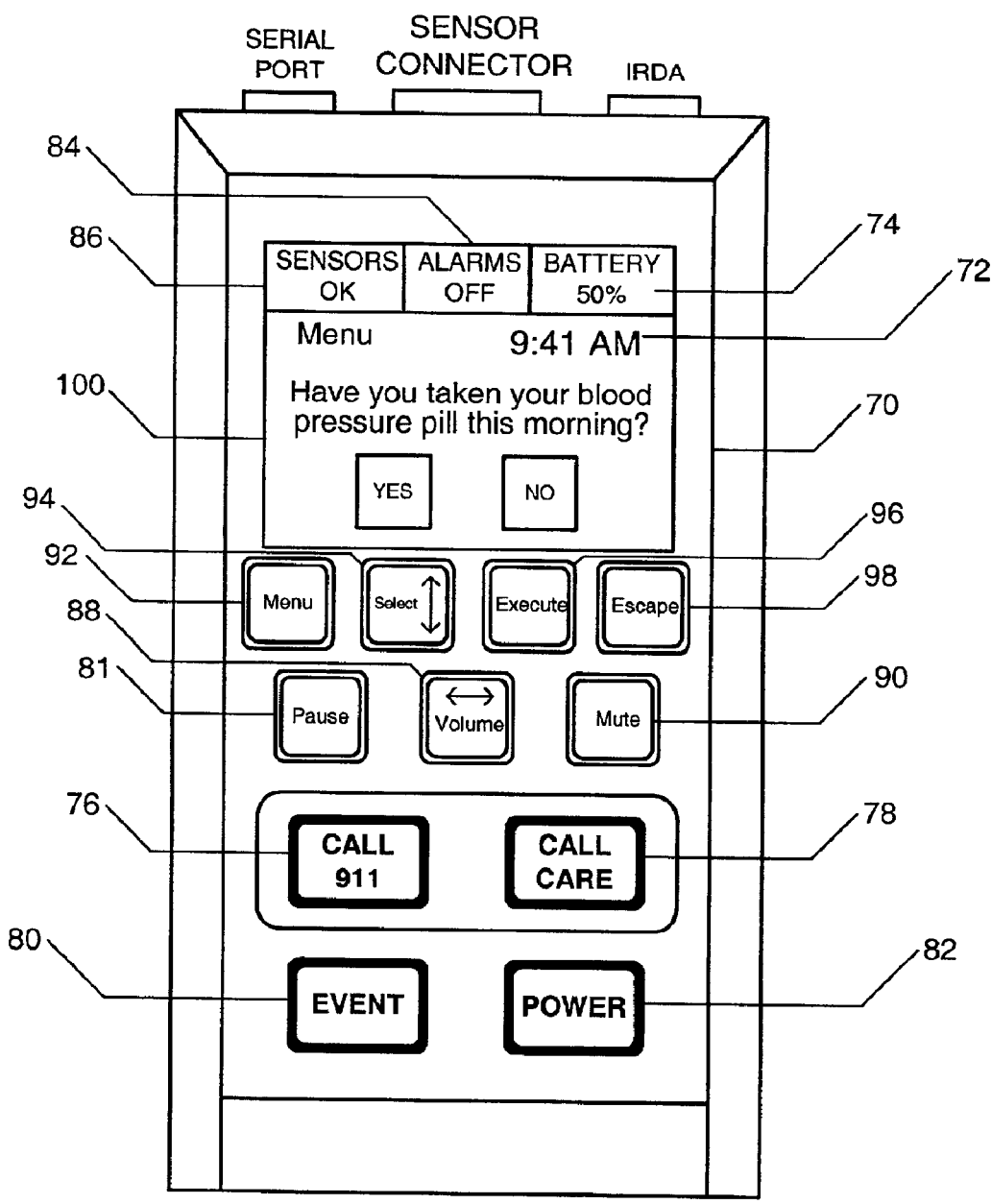
FIG. 4 illustrates a front panel drawing of the Portable Data Monitor.

In FIG. 4, a front panel for the PDM is illustrated. The PDM has a time of day 72 and a battery capacity and signal strength indicators 74 which allow the patient wearing the device to determine if recharging or battery replacement is required. The patient can further determine whether the signal strength of the communications channel is adequate to support reliable communications. The panel 70 is dimensioned to be small and unobtrusive so that the wearer will not be disproportionately burdened by carrying the PDM. The panel has several speed dialing preset buttons that allow emergency calls to 911 76 to be made and calls to the care provider 78 to be made simply by the press of a button. Similarly, if the wearer determines that an "event" has occurred such as faintness, shortness of breath, irregular heartbeat, or other symptoms, this event button 80 can be pressed and a signal generated associated with the event. A power indicator 82 is part of the panel so that the user can determine that power is "on." Sensor lamp 86 is on the panel as well to inform the user whether all sensors are operating or if a sensor has potentially become disconnected or has otherwise malfunctioned. An alarm display 84 together with an audible signal is also present on the control panel so that the patient can have both a visual and audible warning of any alarm condition that might exist.

A Pause button 81 allows the patient to disengage from the PDM for a brief time period. For example, if the patient wants to shower, the wearer depresses the pause button and the operational mode will transition to Idle. The pause button invocation is ignored if an Alarm or Event is in progress. Further, the current profile in effect must allow for the implementation of a pause.

The profile in effect also provides for a pause duration. Once the pause duration is exhausted, the PDM reverts to active mode. An alternative embodiment would allow the PDM wearer to terminate the pause (Idle) mode prior to the allotted pause time allotment. For example, the patient, having finished showering and having re-established the sensor placements, would signal the PDM to become active by depressing the pause button for three seconds, thus causing a transition to the active mode before the pause timeout expired.

Control buttons for volume 88 and mute 90 are located on the face of the PDM. A Menu Button 92 present a list of menu options to the display, along with a cursor. The patient may move the cursor with the Up/Down Select button 94. He may then execute a menu item with a push of the Execute button 96. The Escape button 98 serves a way to back out of a previous menu selection. Obviously, such menu selections could also be used through a "touchscreen" interface.

The panel further contains a bit-mapped array LCD display 100. The display 100 provides a status of the following features: (2) time and date (military or AM/PM format); (2) Current Status of the unit (operational mode, listing of pending alerts and alarms); (3) Voice Call Status; (4) Error Correction Guidance Messages (when appropriate); and a (3) Menu Tool Bar. From the Menu Tool Bar display, the user may configure settings to view: (1) Time format (Military or AM/PM); (2) Sound Volume Up/Down; (3) Current measurement value; (4) Total recording memory capacity and remaining availability; (5) Voice telephone number table entry; (6) Current signal strength; (7) Profile in force with start and stop times; and (8) Battery Capacity. The panel also serves as a touchscreen that enables the user to select a function simply by pressing a portion of the display with his fingertip.

The panel design shown in this FIG. 4 is by way of illustration only. It will be apparent to those skilled in the art that other panel designs, including a touchscreen display, are possible so long as the information is presented and transferred in an easy and useable way for the patient.

As noted above, the communications link between the PDM and the care provider via the PSTN or the Internet is a bi-directional link. Thus requests for data from a workstation located at the care provider's facility can be transmitted through the Internet to the Host which in turn contacts the PDM. Data (real-time or stored) can be transferred from the PDM through the Internet to various databases for analysis or storage. Data from the PDM can be transferred in real-time or from storage through the Internet to other authorized users such as insurance providers. Alarm information is transferred from the PDM to the care provider through the Internet. When a sensor malfunctions or becomes disconnected from the wearer, a "sensor off" signal is sent from the PDM and transferred over the Internet to the medical care provider so that such information is available and so that the patient can be assisted in troubleshooting the cause of the alert. Event information, as described earlier, can be transferred to the medical care provider through the Host. The medical care provider can transmit a communication to disarm or reset alarms in the PDM through the Internet as necessary. Further, protocols relating to the schedule and type of bio-signal to be measured can be sent from the medical provider through the Internet to the PDM. The personal emergency button for use to activate a call from the patient to the medical care provider or 911 emergency operator provides voice communication from the PDM to and from the care provider. Real-time clock resets or any other variations in configuration of the PDM can be transmitted from the medical care provider over the Internet to the PDM.

Figure 5:
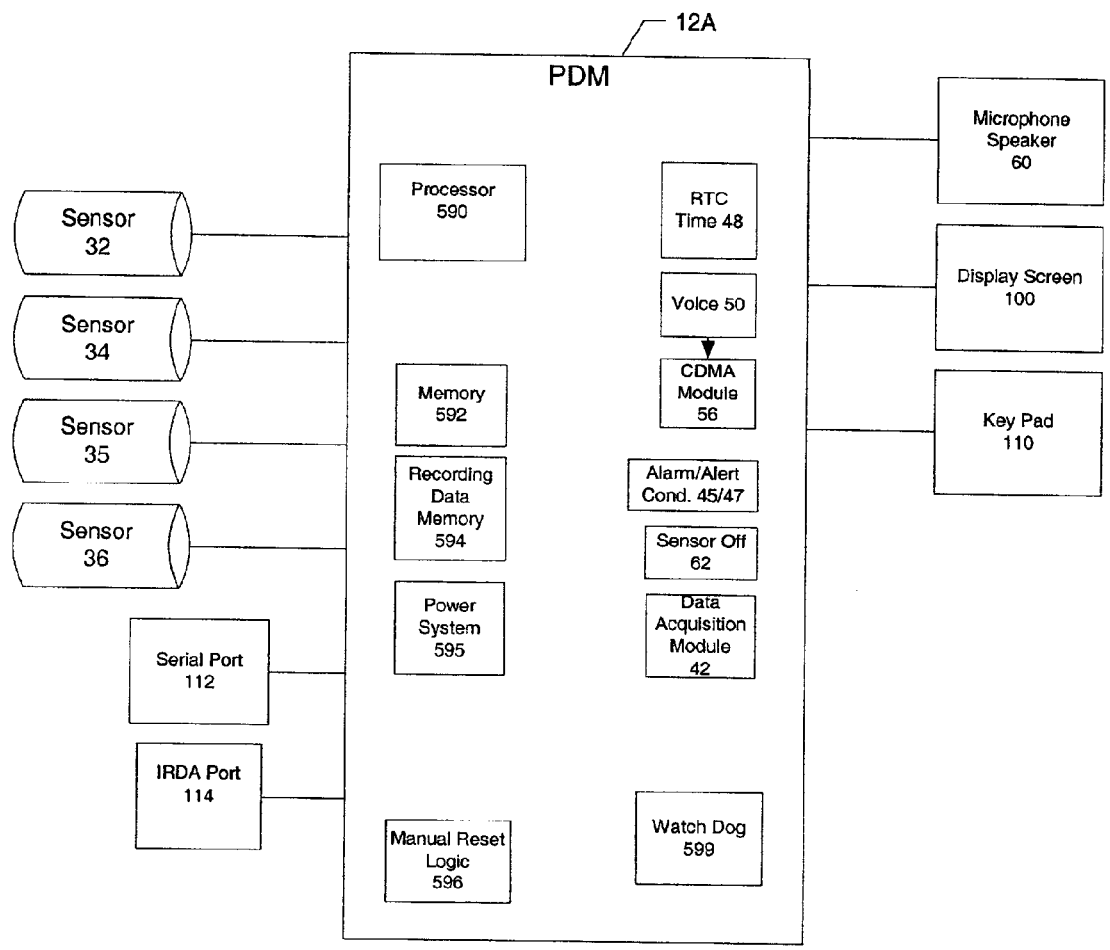
FIG. 5 illustrates the architecture of the Portable Data Monitor.

In FIG. 5, the architecture of the PDM 12A is illustrated. Several systems and components are housed within the PDM 12A. The PDM 12A contains a processor 590, memory 592, recording data memory 594, a power system 595, manual reset logic 596, a watch dog system 599, the CDMA module 56 (previously described in FIG. 2), the data acquisition module 42 (previously described in FIG. 2), input/output means such as Serial port 112, IrDA port 114, microphone/speaker 60, display screen 100 and keypad 110. These systems are electronically connected to and operate the PDM 12.

The processor 590 of the PDM 12 executes operating profiles, setting the PDM to various operational modes, checking internal status, setting alarm or alert conditions, recording data, and sending and receiving audio and text messages. A thirty-two bit microprocessor is used in the PDM. One example of a suitable microprocessor model is the ARM7DTMI made by ARM, Limited. The memory 592 of the PDM is used to store operating instructions executed by the processor 590. Memory 592 further stores patient data, current status, current mode, messaging data, numbers for automatic dialing. One embodiment provides for a memory chip having 32 megabytes of storage used with the present invention, although is not meant as a limitation.

The PDM 12 further houses a power management system, which manages battery power and metering in a manner known to those skilled in the art.

Figure 6:
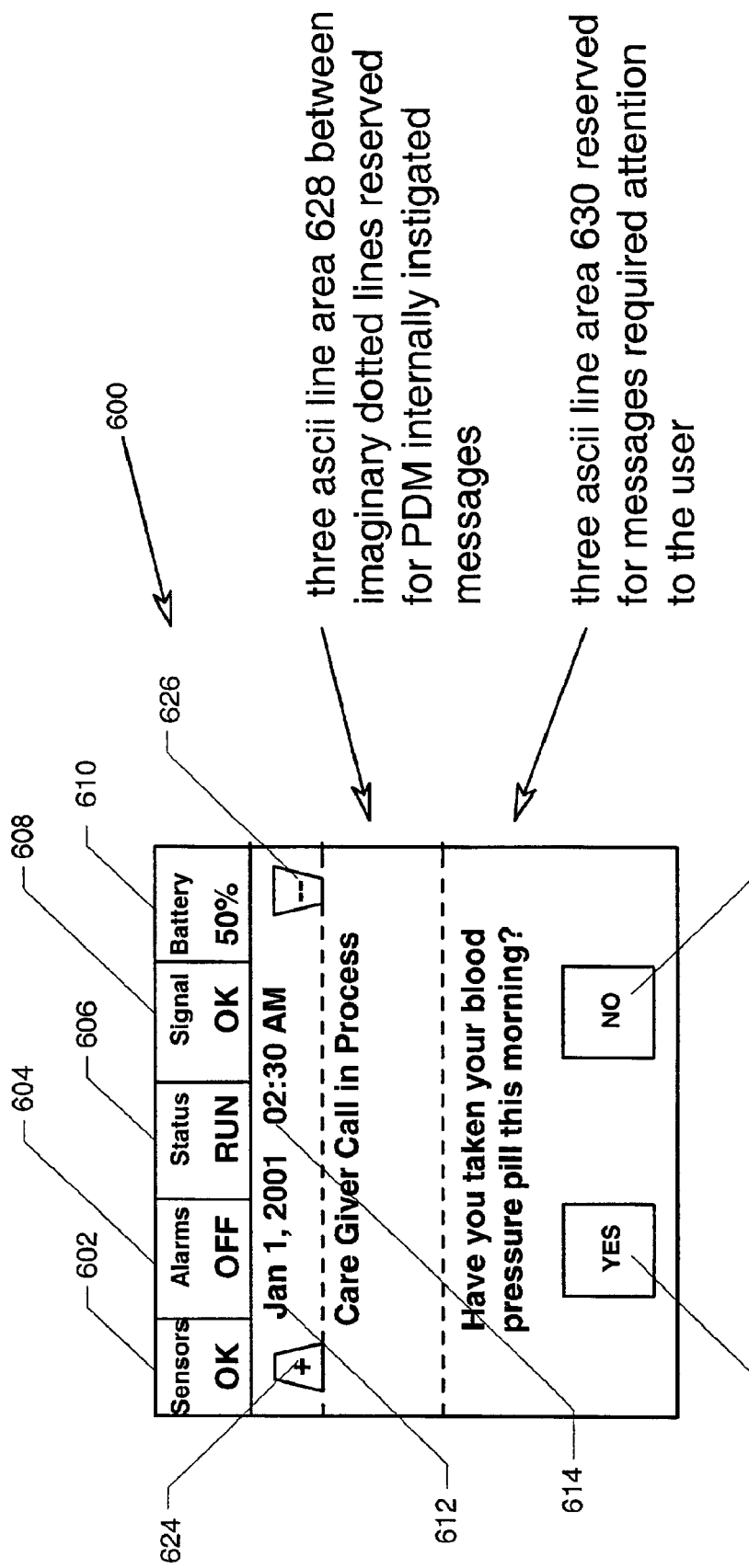
FIG. 6 illustrates a touchscreen of an alternative front panel of the Portable Data Monitor.

In a preferred embodiment, the PDM uses an LCD touch screen display 600 as illustrated in FIG. 6. The following information is displayed on the LCD whenever it is on:

TABLE 1

| SENSORS 602 | | STATUS 606 |
|---|---|---|
| OK | | RUN |
| OFF | | EVENT |
| | | PAUSE |
| ALARMS 604 | SIGNAL 608 | |
| ON | OK | |
| OFF | WEAK | |
| | NONE | |
| BATTERY 610 | DATE 612 | TIME 614 |
| 100% | XX-XX-XX | XX:XX AM |
| 75% | | XX:XX PM |
| 50% | | |
| 25% | | |
| LOW | | |

Two active touchscreen areas on the PDM display are allocated to YES 620 and NO 622 answers. Additional touchscreen areas 624, 626 are allocated for use by the patient to control the volume of the beeps and audio messages. Expansion of these areas into numerical regions is also possible. Additional areas 628 and 630 are used for internally instigated PDM massages and messages requiring the users attention.

An earset tone and a room-audible beep are generated for every message, whether written or spoken. As illustrated in Table 1, a distinctive beep is generated for each class of message. Questions are stored in a messaging profile to be triggered at the pre-set time. Up to 20 questions can be hard-coded into the system. A "Care Manager" picks from pre-selected messages to be sent at a pre-selected time of day. It is also desirable to include a capability for caregivers to ask a custom question over the Internet. Answers to questions are transmitted only when the system does a "post" operation per profile or upon a command from the Care Manager. The system will "post" data whenever patient triggers the "Pause" button, the activation of which will idle the system for 30 minutes after each press.

Voice messaging and phone voice occur simultaneously (additive) in the earset. Pressing any of the buttons on the front panel (including the touchscreen) will cause a short beep tone (Beep #1, external) to be emitted.

Patients using the PDM are instructed to respond to all messages as they are received. The acknowledgement of an instruction (not a question) is by an input of YES 620 by the patient using the touchscreen.

In a preferred embodiment, the bi-directional communication between the sensors and voice data acquisition devices of the PDM and host server on the Internet are accomplished without use of a modem by use of a Sensor and Instrument Interface Communication Module (SIICM), disclosed in co-pending Provisional Application Ser. No. 60/292,065, filed May 18, 2001. The SIICM provides the data acquisition circuitry required to gather various signals from sensors for a variety data (including physiologic data from the human body or data from remote non-medical monitoring instrumentation) and to condition those signals for interface to a variety of possible digital cellular phone or other wireless communication modules which are used to transmit these data into the digital cellular network for distribution on the Internet.

Figure 7:
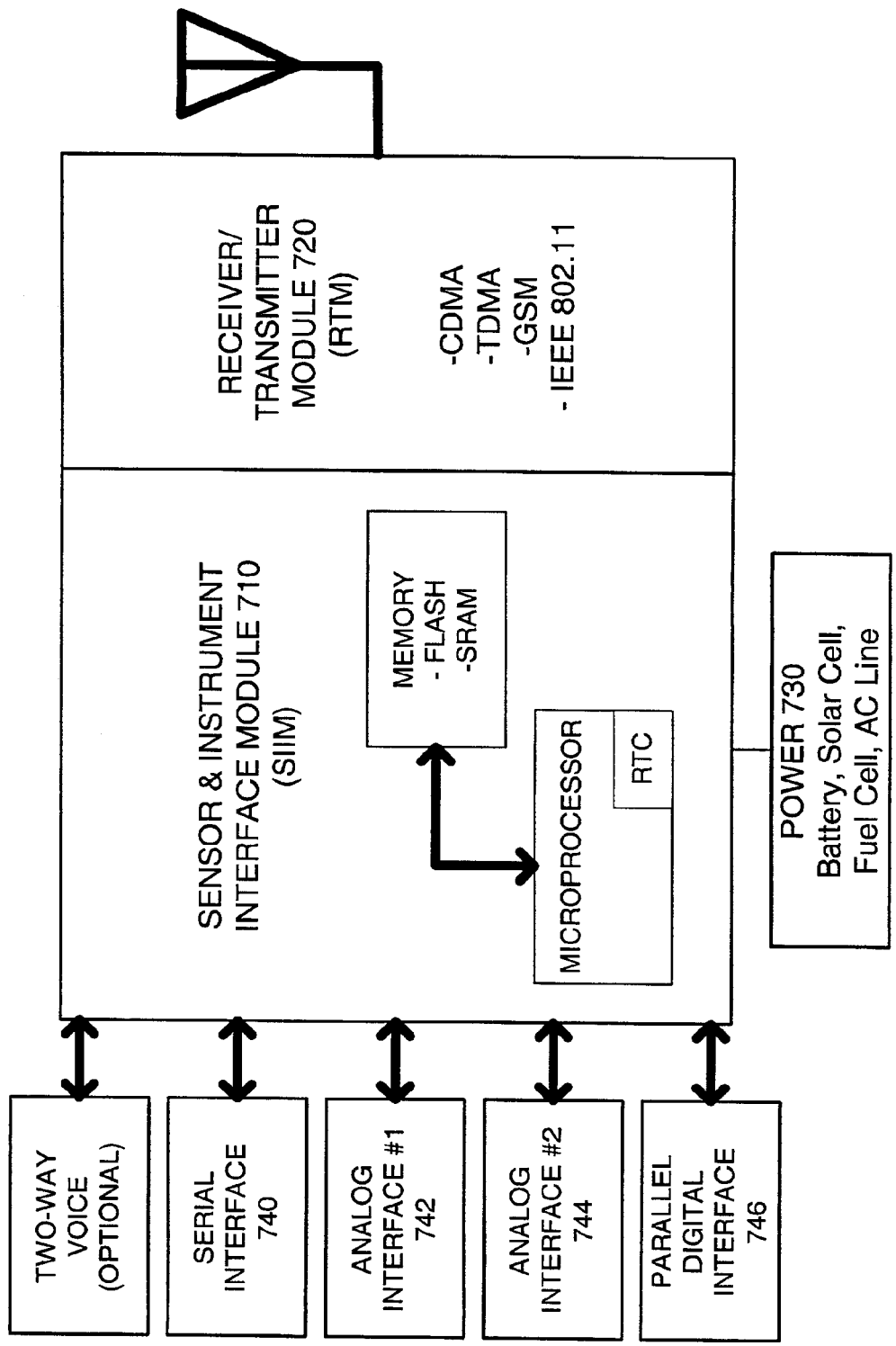
FIG. 7 illustrates a schematic diagram of a preferred SIICM of the present invention.

FIG. 7 is a sketch of the essential features of a Wireless Data Communicator, comprised of a Sensor Instrument Interface Module 710 (SIIM) connected to a Receiver/

Transmitter Module 720 (RTM) which provides the wireless interface to the Internet. The sensors, as noted above, can be any of a wide variety of physical and biosensors generally used to detect signals or variables from the (1) human body, (2) instruments, (3) equipment, (4) environment, etc. Sensors and instruments used in measuring clinically relevant data are of particular interest for use in this system. Such data include electrocardiogram, temperature, respiration, acceleration, audio, oximetry, blood glucose, body weight, capnogram, geographic position (GPS), blood pressure, keyboard, pipeline pressure, etc. The RTM can contain a variety of wireless communication protocols; e.g., CDMA, TDMA, GSM, IEEE802.11, etc.

Power 730 can be supplied from a variety of sources that include batteries, solar cells, fuel cells, AC lines, etc. Specialized sensor interface modules can be plugged into ports 740–746 of the SIICM to interface with a wider variety of sensors, instruments, or equipment.

The SIICM is designed to recognize the characteristics of the sensor, instrument, or equipment to which it is attached and to encode the transmitted data in a manner that will allow a central Internet database to interpret and display the data. Since the wireless data communicator has two-way digital communications capability, a smart sensor interface (similar to "plug and play") can be implemented either in the memory of the SIIM or the SIICM can be configured remotely by commands from the central Internet database to recognize the interface.

The preferred communication from of the present invention is disclosed in co-pending Provisional Application Ser. No. 60/292,068, filed May 18, 2001. In this preferred system, a high-level Extensible Markup Language (XML) structure and communication process is used, as disclosed below.

In this embodiment, the patient data monitoring is implemented for wireless communications between the Host (PhDx) and the remote PDM (PDM2000) by using an XML message schema, an XML transaction schema for scheduled sensor data, and an XML transaction schema for acknowledgement (ACK) data.

XML Message Schema

The XML schema used to validate the high-level XML message structure is shown below:

```
<?xml    version="1.0"?>
<Schema
        name="PhDxPDM2000MSGSchema"
        xmlns="urn:schemas-microsoft-com:xml-data"
        xmlns:dt="urn:schemas-microsoft-com:datatypes">
        <ElementType name='MSG' content='eltOnly'>
            <element type='MID'   minOccurs='1' maxOccurs='1'/>
            <element type='MDT'   minOccurs='1' maxOccurs='1'/>
            <element type='MTY'   minOccurs='1' maxOccurs='1'/>
            <element type='CMM'   minOccurs='1' maxOccurs='1'/>
            <element type='CID'   minOccurs='1' maxOccurs='1'/>
            <element type='EID'   minOccurs='1' maxOccurs='1'/>
            <element type='RID'   minOccurs='1' maxOccurs='1'/>
            <element type='TCT'   minOccurs='1' maxOccurs='1'/>
            <element type='TRA'   minOccurs='1' maxOccurs='*'/>
        </ElementType>
        <ElementType name='MID'   content='textOnly'
                                  dt:type='int'/>
        <ElementType name='MDT'   content='textOnly'
                                  dt:type='dateTime'/>
        <ElementType name='MTY'   content='textOnly'
                                  dt:type='int'/>
        <ElementType name='CMM'   content='textOnly'
                                  dt:type='int'/>
```

```
        <ElementType name='CID'   content='textOnly'
                                  dt:type='int'/>
        <ElementType name='EID'   content='textOnly'
                                  dt:type='int'/>
        <ElementType name='RID'   content='textOnly'
                                  dt:type='int'/>
        <ElementType name='TCT'   content='textOnly'
                                  dt:type='int'/>
        <ElementType name='TRA'   content='eltOnly'>
            <element type='TID'   minOccurs='1' maxOccurs='1'/>
            <element type='TCD'   minOccurs='1' maxOccurs='1'/>
            <element type='TVL'   minOccurs='1' maxOccurs='1'/>
        </ElementType>
        <ElementType name='TID'   content='textOnly'
                                  dt:type='int'/>
        <ElementType name='TCD'   content='textOnly'
                                  dt:type='int'/>
        <ElementType name='TVL'   content='eltOnly'>
</Schema>
```

XML Transaction Schema—Scheduled Sensor Data

The XML schema used to validate the lower-level XML transaction structure for a scheduled sensor data post is shown below. A separate schema exists for each of the different transaction types.

```
<?xml    version="1.0"?>
<Schema
        name="PDM2000Schema__POSTSCHEDULEDSENSORDATA"
        xmlns="urn:schemas-microsoft-com:xml-data"
        xmlns:dt="urn:schemas-microsoft-com:datatypes">
        <ElementType name='TVL' content='eltOnly'>
            <element type='TVO'   minOccurs='1' maxOccurs='1'/>
            <element type='TVT'   minOccurs='1' maxOccurs='1'/>
            <element type='TVH'   minOccurs='1' maxOccurs='1'/>
            <element type='DSS'   minOccurs='1' maxOccurs='1'/>
            <element type='DES'   minOccurs='1' maxOccurs='1'/>
        </ElementType>
        <ElementType name='TVO'   content='textOnly'
                                  dt:type='int'/>
        <ElementType name='TVT'   content='textOnly'
                                  dt:type='float'/>
        <ElementType name='TVH'   content='textOnly'
                                  dt:type='int'/>
        <ElementType name='DSS'   content='textOnly'
                                  dt:type='bin.hex'/>
        <ElementType name='DES'   content='eltOnly'
            <element type='CCC'   minOccurs='1' maxOccurs='1'/>
            <element type='CBC'   minOccurs='1' maxOccurs='1'/>
            <element type='TSI'   minOccurs='1' maxOccurs='1'/>
            <element type='OSI'   minOccurs='1' maxOccurs='1'/>
            <element type='PAC'   minOccurs='1' maxOccurs='1'/>
            <element type='CER'   minOccurs='1' maxOccurs='1'/>
            <element type='PRF'   minOccurs='1' maxOccurs='1'/>
            <element type='MOD'   minOccurs='1' maxOccurs='1'/>
            <element type='PAU'   minOccurs='1' maxOccurs='1'/>
        </ElementType>
        <ElementType name='CCC'   content='textOnly'
                                  dt:type='int'/>
        <ElementType name='CBC'   content='textOnly'
                                  dt:type='int'/>
        <ElementType name='TSI'   content='textOnly'
                                  dt:type='int'/>
        <ElementType name='OSI'   content='textOnly'
                                  dt:type='int'/>
        <ElementType name='PAC'   content='textOnly'
                                  dt:type='int'/>
        <ElementType name='CER'   content='textOnly'
                                  dt:type='int'/>
        <ElementType name='PRF'   content='textOnly'
                                  dt:type='int'/>
        <ElementType name='MOD'   content='textOnly'
                                  dt:type='int'/>
        <ElementType name='PAU'   content='textOnly'
                                  dt:type='int'/>
</Schema>
```

EXAMPLE

Scheduled Sensor Data Post

The scheduled sensor data transaction posts the personal sensor measurements (taken as scheduled by the PDM's internal sensor profile settings) from the PDM to the server. As shown in the table below, this transaction contains the sensor values, the device standard status, and the device extended status.

The full set of message tags is as follows:

```
<MSG>
    <MID>MESSAGE_ID</MID>
    <MDT>MESSAGE_DATE</MDT>
    <MTY>DATAPOSTSET</MTY>
    <CMM>COMM_MODE</CMM>
    <CID>CLIENT_ID</CID>
    <EID>EXTERNAL_ID</EID>
    <RID>0</RID>
    <TCT>1</TCT>
    <TRA>
        <TID>TRANSACTION_ID</TID>
        <TCD>SCHEDULED_SENSOR_DATAPOST</TCD>
        <TVL>
            <TVO>100</TVO>
            <TVT>98.6</TVT>
            <TVH>75</TVH>
            <DSS>PDM_STANDARD_STATUS_16_BYTE_RECORD</DSS>
            <DES>
                <CCC>0</CCC>
                <CBC>0</CBC>
                <TSI>0</TSI>
                <OSI>0</OSI>
                <PAC>0</PAC>
                <CER>0</CER>
                <PRF>0</PRF>
                <MOD>0</MOD>
                <PAU>0</PAU>
            </DES>
        </TVL>
    </TRA>
</MSG>
```

XML Transaction Schema—Acknowledgement (ACK)

The XML schema used to validate the lower-level XML transaction structure for a message acknowledgement (ACK) is shown below. A separate schema exists for each of the different transaction types.

```
<?xml    version="1.0"?>
<?xml    version="1.0"?>
<Schema
    name="PDM2000Schema_ACK"
    xmlns="urn:schemas-microsoft-com:xml-data"
    xmlns:dt="urn:schemas-microsoft-com:datatypes">
    <ElementType name='TVL' content='eltOnly'>
        <element type='VAL' minOccurs='1' maxOccurs='1'/>
    </ElementType>
        <ElementType name='VAL' content='textOnly'
            dt:type='string'/>
</ Schema>
```

EXAMPLE

The Acknowledge (ACK) Message

The Acknowledge (ACK) message is defined as follows:

```
<MSG>
    <MID>MESSAGE_ID</MTD>
    <MDT>MESSAGE_DATE</MDT>
    <MTY>ACK</MTY>
    <CNM>COMM_MODE</CMM>
    <CID>CLIENT_ID</CID>
    <EID>EXTERNAL_ID</EID>
    <RTD>REFERENCE_MESSAGE_ID</RID>
    <TCT>1</TCT>
    <TRA>
        <TID>TRANSACTION_ID</TID>
        <TCD>ACKTRAN</TCD>
        <TVL>
            <VAL>VALUE</VAL>
        </TVL>
    <TRA>
</MSG>
```

Message Types and Communication Modes Data Flow

The following tables 2–3 enumerate by message type and communications mode each of the allowable transactions and their responses. Items marked "N/A" in the comment column will not be implemented in PDM2000 and are included here only for sake of completeness.

TABLE 2

PDM TO SERVER

| MSG TYPE | COMM MODE | TRAN CODE | RESPONSE | COMMENT |
|---|---|---|---|---|
| DataPostSet (PDM to Server) | | | | |
| | Cont | | | N/A* |
| | Stop | | | N/A* |
| | More | | ACK/NAK | |
| | None | | ACK/NAK | |
| | | Post scheduled sensor data | | |
| | | Post requested sensor data | | |
| | | Post exception sensor data | | |
| | | Post scheduled messaging response | | |
| | | Post requested messaging response | | N/A* |
| | | Post protocol and messaging profile block | | |
| | | Protocol settings | | |
| | | Messaging profile settings | | |
| | | CRC | | |
| | | Post operational mode and status | | |
| | | Post non-profile device settings | | N/A* |
| | | Post call statistics | | N/A* |
| | | Post exception other data (multiple types) | | e.g. profile failed |
| | | Post scheduled sensor data failure | | |
| | | Post requested sensor data failure | | |
| | | Post scheduled messaging item failure | | |
| | | Post requested messaging item failure | | N/A* |
| | | (Note: Alarms not in COPD) | | |
| Inquiry (PDM to Server) | | | | |
| | Cont | InstructionSet | | |
| | Stop | | | N/A* |
| | More | | | N/A* |
| | None | | | N/A* |
| | | Inquiry transaction | | |
| | | (Note: PDM never sends an Inquiry if it has data to send itself) | | |
| ACK - Message Confirmation - (PDM to Server) | | | | |
| | Cont | InstructionSet | | Response to InstructionSet + More |
| | Stop | | | N/A* |
| | More | ACK + Cont | | PDM now has data to send |

TABLE 2-continued

PDM TO SERVER

| MSG TYPE | COMM MODE | TRAN CODE | RESPONSE COMMENT |
|---|---|---|---|
| | None | Goodbye | Response to InstructionSet + None |
| | | Confirmation transaction | |
| NAK - Message Failure - (PDM to Server) | | | |
| | Cont | Resend message | Try to resend reference message |
| | Stop | ACK + More/ACK + None | Stop sending reference message Server checks for other messages |
| | More | ACK + Cont | PDM now has data to send |
| | None | | N/A* |
| | Failure transaction | | |
| | (Note: Error information is in Transaction Value) | | |
| Goodbye (PDM to Server) | | | |
| | Cont | | N/A* |
| | Stop | Goodbye | End message session |
| | More | | N/A* |
| | None | | N/A* |
| | Goodbye transaction | | |

TABLE 3

SERVER TO PDM

| MSG TYPE | COMM MODE | TRAN CODE | RESPONSE COMMENT |
|---|---|---|---|
| InstructionSet (Server to PDM) | | | |
| | Cont | | N/A* |
| | Stop | | N/A* |
| | More | ACK/NAK | |
| | None | ACK/NAK | |
| | Set protocol and messaging profile block | | |
| | Protocol settings | | |
| | Messaging profile settings | | |
| | CRC | | |
| | Send protocol and messaging profile block | | |
| | Send requested sensor data | | |
| | Perform requested messaging item | | N/A* |
| | Set non-profile device settings | | N/A* |
| | Send non-profile device settings data | | N/A* |
| | Set operational mode & current status | | |
| | Send operational mode & current status | | |
| | Set call statistics (reset) | | N/A* |
| | Send call statistics | | N/A* |
| | Set no server message pending | | Server has no messages to send |
| ACK - Message Confirmation (Server to PDM) | | | |
| | Cont | DataPostSet | Response to DataPostSet + More |
| | Stop | | N/A* |
| | More | Inquiry (usually) | Response to DataPostSet + None Server has messages |
| | None | Goodbye (usually) | Response to DataPostSet + None Server has no messages |
| | Confirmation transaction | | |
| | (Note: PDM ends all sessions. Server interrupt not used) | | |
| NAK - Message Failure (Server to PDM) | | | |
| | Cont | | N/A* |
| | Stop | | N/A* |
| | More | Resend message or Stop | Server has messages |
| | None | Resend message or Stop | Server has no messages |
| | Failure transaction | | |
| | (Note: Error information is in Transaction Value) | | |

TABLE 3-continued

SERVER TO PDM

| MSG TYPE | COMM MODE | TRAN CODE | RESPONSE COMMENT |
|---|---|---|---|
| Goodbye (Server to PDM) | | | |
| | Cont | No response required | Normal end of message session |
| | Stop | | N/A* |
| | More | | N/A* |
| | None | | N/A* |
| | Goodbye transaction | | |
| | (Note: PDM ends all sessions. Server interrupt not used) | | |

Although, in a typical embodiment, the PDM of the present invention will be patient-worn and will monitor sensors attached to the patient, the PDM can also interface external devices that a patient can interact with for sensing medically relevant data, such as blood glucose monitors, scales, etc. The PDM can interface with these external devices in any known manner, such as by a wired connection that plugs in to the PDM or by wireless means, such as Bluetooth, IrDA, and IEEE 802.11 protocols.

In a basic embodiment, voice communication capabilities and the PSTN link can be omitted. In another embodiment, voice communications can be provided between the patient and caregiver by voice-over-IP technology in order to eliminate the PSTN link.

A Wireless Internet Bio-telemetry Monitoring System has now been illustrated. It is important to note that, while a particular wireless protocol was described in the preferred embodiment (i.e., CDMA) this is not meant as a limitation. For example, other protocols for communication in a wireless network (such as a GSM, PCS or TDMA) will be equally suitable for use with the present invention. It is also anticipated that other types of wireless networks will also be suitable, such as satellite networks and wireless local loop networks. The requirement is that there be two-way communication with the PDM and that Internet connectivity flow as part of the communication system to allow interaction between health care provider and the patient via voice and via the Internet. It will be apparent to those skilled in the art that other variations in, for example and without limitation, the type of network, the type of bio-sensor, and the configuration of the patient monitor can be accomplished without departing from the scope of the invention as disclosed.

We claim:

1. A system for remotely monitoring patient variables comprising:

at least one patient-wearable, multi-variable sensor means for acquiring medically relevant data from a patient;

a patient-wearable monitoring unit connected to the sensor;

said patient-wearable monitoring unit comprising a processor means for formatting sensor data from said patient into Extensible Markup Language (XML) and a wireless communication device connected to a first wireless network, wherein said first wireless network includes means adapted to send and receive communications over the Internet and a second network;

a Host data archive connected to the Internet to communicate with a plurality of the patient-wearable monitoring units and archive data using XML;

a plurality of medical care provider terminal means connected to the second network for communication in a bi-directional manner over said first and second network between each medical care provider and the patient-wearable monitoring unit of a patient under the medical care provider's care, and wherein said plurality of medical care provider terminals are further connected to the Internet for bi-directional XML data communication with said Host data archive.

2. The system for remotely monitoring patient variables of claim 1 wherein the communication with the patient-wearable monitoring unit is bi-directional XML data communication.

3. The system for remotely monitoring patient variables of claim 2 wherein the bi-directional XML data communication further comprises instructions from the medical care provider terminal to change configurable program instructions in the processor of the patient-wearable monitoring unit.

4. The system for remotely monitoring patient variables of claim 3 wherein the instructions to change configurable program instructions comprises instructions to change alarm limits.

5. The system for remotely monitoring patient variables of claim 3 wherein the instructions to change configurable program instructions comprises instructions to change data collection parameters for the at least one patient-wearable sensor.

6. The system for remotely monitoring patient variables of claim 1 wherein the communication with the patient-wearable monitoring unit is bi-directional voice communication.

7. The system for remotely monitoring patient variables of claim 6 wherein the bi-directional voice communications comprises voice-over-IP communications with a medical care provider professional.

8. The system for remotely monitoring patient variables of claim 7 wherein the at least one sensor further comprises a microphone and a speaker for transmitting voice communications.

9. The system for remotely monitoring patient variables of claim 7 wherein voice messaging is assigned priority by the processor according to the type of message being sent.

10. The system for remotely monitoring patient variables of claim 6, further comprising a second network connected to said first wireless network and said medical care provider terminal means to transmit bi-directional voice communications.

11. The system for remotely monitoring patient variables of claim 10 wherein the second network is a PSTN.

12. The system for remotely monitoring patient variables of claim 1 wherein said at least one sensor is wirelessly connected to said patient-wearable monitoring unit.

13. The system for remotely monitoring patient variables of claim 1 wherein said at least one sensor is a device for monitoring physiologic, biochemical or biometric variables.

14. The system for remotely monitoring patient variables of claim 1 wherein the processor of the patient-wearable monitoring unit further comprises a conversion means for adapting data transmission for multiple platforms.

15. The system for remotely monitoring patient variables of claim 14 wherein the conversion means adapts data transmission for CDMA Periodic Post, CDMA Host Request, and RS232 Slave Request platforms.

16. The system for remotely monitoring patient variables of claim 14 wherein the conversion means adapts data transmission for multiple platforms in an encrypted format.

17. The system for remotely monitoring patient variables of claim 1, wherein said Host data archive comprises a Host server connected to the Internet for communicating with the patient-wearable monitoring unit and the medical care provider terminal means in a bi-directional manner.

18. The system for remotely monitoring patient variables of claim 17 wherein the patient-wearable monitoring unit includes instructions to post data to the Host server at a web site.

19. The system for remotely monitoring patient variables of claim 17 wherein the Host server includes instructions to initiate a voice call to a specific patient-wearable monitoring unit.

20. The system for remotely monitoring patient variables of claim 17 including means for the patient to initiate a voice call to a medical care provider.

21. The system for remotely monitoring patient variables of claim 17 including means for the patient to initiate a voice call to 911.

22. The system for remotely monitoring patient variables of claim 17 wherein the Host server includes instructions to periodically retrieve continuous real-time waveform data from the patient-wearable monitoring unit.

23. The system for remotely monitoring patient variables of claim 17 wherein the patient-wearable monitoring unit includes instructions to store and execute an operating profile.

24. The system for remotely monitoring patient variables of claim 23 including means for the operating file to be downloaded from the Host server.

25. The system for remotely monitoring patient variables of claim 23 wherein the operating file further comprises a control block assigning time periods and cycles for each monitored patient variable.

26. The system for remotely monitoring patient variables of claim 23 wherein the operating file further comprises an enable/disable instruction for each monitored patient variable.

27. The system for remotely monitoring patient variables of claim 23 wherein the patient-wearable monitoring unit includes an operational mode.

28. The system for remotely monitoring patient variables of claim 27 wherein the operational mode is selected from the group consisting of Idle Mode, Active Mode, Alarm Mode, and Event Mode.

29. The system for remotely monitoring patient variables of claim 23 wherein the patient-wearable monitoring unit includes instructions to store internal status indicators of the patient-wearable monitoring unit at all times.

30. The system for remotely monitoring patient variables of claim 29 further comprising the internal status indicators of measurement status, alarm status, alert status current operation mode, current operating profile, communication signal status, and memory status.

31. The system for remotely monitoring patient variables of claim 17 including a power management program for execution by the processor.

32. The system for remotely monitoring patient variables of claim 17, further comprising a touchscreen on said patient-wearable monitoring unit and instructions for said processor to provide bi-directional text messaging between said patient-wearable monitoring unit and said Host server.

33. The system for remotely monitoring patient variables of claim 1 wherein the (patient-wearable monitoring unit is connected to a personal computer and the personal computer is connected to the Internet.

34. The system for remotely monitoring patient variables of claim 33 wherein a service computer is connected to the Internet and includes software to perform testing and repair of the patient-wearable monitoring unit over the second network.

35. The system for remotely monitoring patient variables of claim 33 wherein the service computer includes instructions to download software programs to the patient-wearable monitoring unit over the Internet.

36. The system for remotely monitoring patient variables of claim 1 wherein the processor includes logic and instructions to set an Alarm mode.

37. The system for remotely monitoring patient variables of claim 36 wherein the processor sets the Alarm mode when a measurement exceeds set limits.

38. The system for remotely monitoring patient variables of claim 36 wherein the processor sets the Alarm mode when a measurement is not received by the Host server.

39. The system for remotely monitoring patient variables of claim 1 wherein the patient-wearable monitoring unit includes instructions to contact the Host, which in turn includes instructions to contact the medical care provider in response to an Alarm mode being set.

40. A method for remotely monitoring patient variables comprising:
supplying a plurality of patients with a patient-wearable monitoring unit connected to at least one patient-wearable, multi-variable sensor that acquires medically relevant data from the patient; wherein each patient-wearable monitoring unit includes a processor formatting said data from said patient into Extensible Markup Language (XML) and further includes a wireless communication device connecting said patient-wearable monitoring unit to a first wireless network;
said first wireless network sending and receiving communications over the Internet and a second network;
each monitoring unit sending and receiving XML data communications over the first wireless network with a Host data archive connected to the Internet; and
the first wireless network sending and receiving communications from each patient's medical care provider over the second network so as to communicate in a bi-directional manner with the monitoring unit;
and each patient's medical care provider sending and receiving XML data communications over the Internet with said Host data archive.

41. The method for remotely monitoring patient variables of claim 40 wherein the communication with the monitoring unit is bi-directional XML data communication.

42. The method for remotely monitoring patient variables of claim 41 wherein the bi-directional XML data communication is from a medical care provider terminal and changes configurable program instructions in the processor of the monitoring unit.

43. The method for remotely monitoring patient variables of claim 42 wherein the change to configurable program instructions comprises instructions to change alarm limits or data collection parameters.

44. The method for remotely monitoring patient variables of claim 40 wherein the communication with the monitoring unit is bi-directional voice communication selected from voice-over-IP via the Internet or voice communication over a second network between said first wireless network and the medical care provider.

45. The method for remotely monitoring patient variables of claim 44 wherein said second network is a PSTN.

46. The method for remotely monitoring patient variables of claim 44 wherein said at least one sensor further comprises a microphone and a speaker used for transmitting voice communications.

47. The method for remotely monitoring patient variables of claim 44 wherein voice messaging is assigned priority by the processor according to the type of message being sent.

48. The method for remotely monitoring patient variables of claim 40 further comprising wirelessly connecting said at least one sensor to said monitoring unit.

49. The method for remotely monitoring patient variables of claim 40 further comprising selecting said at least one sensor from devices for monitoring physiologic, biochemical or biometric variables.

50. The method for remotely monitoring patient variables of claim 40 wherein the processor of the monitoring unit further adapts data transmission for multiple platforms.

51. The method for remotely monitoring patient variables of claim 50 wherein the multiple platforms are CDMA Periodic Post, CDMA Host Request, and RS232 Slave Request platforms.

52. The method for remotely monitoring patient variables of claim 50 wherein the processor adapts data transmission for multiple platforms in an encrypted format.

53. The method for remotely monitoring patient variables of claim 40 further comprising connecting a Host server to the second network for communicating with the monitoring unit and a medical care provider terminal in a bi-directional manner.

54. The method for remotely monitoring patient variables of claim 53 wherein the monitoring unit posts data to the Host server at a web site.

55. The method for remotely monitoring patient variables of claim 53 wherein the Host server initiates a voice call to a specific monitoring unit.

56. The method for remotely monitoring patient variables of claim 53 wherein the patient initiates a voice call to a medical care provider.

57. The method for remotely monitoring patient variables of claim 53 wherein the patient initiates a voice call to 911.

58. The method for remotely monitoring patient variables of claim 53 wherein the Host periodically retrieves continuous real-time waveform data from the monitoring unit.

59. The method for remotely monitoring patient variables of claim 53 wherein the monitoring unit stores and executes an operating profile.

60. The method for remotely monitoring patient variables of claim 59 wherein the operating file is downloaded from the Host server.

61. The method for remotely monitoring patient variables of claim 59 wherein the operating file further includes a control block assigning time periods and cycles for each monitored patient variable.

62. The method for remotely monitoring patient variables of claim 59 wherein the operating file further includes an enable/disable instruction for each monitored patient variable.

63. The method for remotely monitoring patient variables of claim 53 further comprising setting the monitoring unit to an operational mode.

64. The method for remotely monitoring patient variables of claim 63 wherein the operational mode is selected from the group consisting of Idle Mode, Active Mode, Alarm Mode, and Event Mode.

65. The method for remotely monitoring patient variables of claim 53 wherein the monitoring unit stores internal status indicators of the monitoring unit at all times.

66. The method for remotely monitoring patient variables of claim 65 further comprising storing the internal status indicators of measurement status, alarm status, alert status current operation mode, current operating profile, communication signal status, and memory status.

67. The method for remotely monitoring patient variables of claim 53 wherein the processor executes a power management program.

68. The method for remotely monitoring patient variables of claim 53, further comprising providing a touchscreen on said monitoring unit and instructions for said processor to provide bi-directional text messaging between said monitoring unit and said Host server.

69. The method for remotely monitoring patient variables of claim 40 further comprising connecting the monitoring unit to a personal computer and the personal computer to the Internet.

70. The method for remotely monitoring patient variables of claim 69 further comprising connecting a service computer to the Internet and performing testing and repair of the monitoring unit over the second network.

71. The method for remotely monitoring patient variables of claim 70 wherein the service computer downloads software programs to the monitoring unit over the Internet.

72. The method for remotely monitoring patient variables of claim 40 wherein the processor sets an Alarm mode.

73. The method for remotely monitoring patient variables of claim 72 wherein the processor sets the Alarm mode when a measurement exceeds set limits.

74. The method for remotely monitoring patient variables of claim 40 wherein the monitoring unit contacts the Host server, which in turn contacts the medical care provider in response to an Alarm mode being set.

75. The method for remotely monitoring patient variables of claim 74 wherein the processor sets the Alarm mode when a measurement is not received by the Host server.

* * * * *